US010906941B2

(12) United States Patent
Kim et al.

(10) Patent No.: US 10,906,941 B2
(45) Date of Patent: Feb. 2, 2021

(54) METHODS OF INDUCING AN IMMUNE RESPONSE AGAINST HIV-1 USING RECOMBINANT ENVELOPES WITH IMPROVED COVERAGE

(71) Applicants: DUKE UNIVERSITY, Durham, NC (US); THE GOVERNMENT OF THE UNITED STATES AS REPRESENTED BY THE SECRETARY OF THE ARMY, Fort Detrick, MD (US); THE HENRY M. JACKSON FOUNDATION FOR THE ADVANCEMENT OF MILITARY MEDICINE, INC., Bethesda, MD (US); LOS ALAMOS NATIONAL SECURITY, LLC, Los Alamos, NM (US)

(72) Inventors: Jerome Kim, Fort Detrick, MD (US); Morgane Rolland, Bethesda, MD (US); Bette T. Korber, Los Alamos, NM (US); Barton F. Haynes, Durham, NC (US)

( * ) Notice: Subject to any disclaimer, the term of this patent is extended or adjusted under 35 U.S.C. 154(b) by 0 days.

(21) Appl. No.: 14/784,496

(22) PCT Filed: Apr. 15, 2014

(86) PCT No.: PCT/US2014/034126
§ 371 (c)(1),
(2) Date: Oct. 14, 2015

(87) PCT Pub. No.: WO2014/172335
PCT Pub. Date: Oct. 23, 2014

(65) Prior Publication Data

US 2016/0115205 A1 Apr. 28, 2016

Related U.S. Application Data

(60) Provisional application No. 61/812,093, filed on Apr. 15, 2013.

(51) Int. Cl.

| | |
|---|---|
| *C07K 14/005* | (2006.01) |
| *A61K 39/12* | (2006.01) |
| *C12N 7/00* | (2006.01) |
| *A61K 39/00* | (2006.01) |

(52) U.S. Cl.
CPC ............ *C07K 14/005* (2013.01); *A61K 39/12* (2013.01); *C12N 7/00* (2013.01); *A61K 2039/70* (2013.01); *C12N 2740/16122* (2013.01); *C12N 2740/16134* (2013.01)

(58) Field of Classification Search

CPC .................. C07K 14/005; A61K 39/12; C12N 2740/16134; C12N 2740/16122

See application file for complete search history.

(56) References Cited

U.S. PATENT DOCUMENTS

| | | | | |
|---|---|---|---|---|
| 7,847,085 | B2 | 12/2010 | Zolla-Pazner et al. | |
| 7,901,690 | B2 | 3/2011 | Lu et al. | |
| 9,044,420 | B2 * | 6/2015 | Dubensky, Jr. .... | A61K 39/0011 |
| 2013/0273103 | A1 * | 10/2013 | Liao ...................... | A61K 39/21 424/208.1 |
| 2014/0248311 | A1 * | 9/2014 | Kim ...................... | A61K 39/21 424/208.1 |

FOREIGN PATENT DOCUMENTS

| | | |
|---|---|---|
| WO | WO 2011/035082 | 3/2011 |
| WO | WO 2012/047267 | 4/2012 |
| WO | WO 2013/006688 | 1/2013 |
| WO | WO 2013/085550 | 6/2013 |
| WO | WO 2013/134293 | 9/2013 |

OTHER PUBLICATIONS

Rolland, M., et al., Oct. 2012, Increased HIV-1 vaccine efficacy against viruses with genetic signatures in Env V2, Nature 490(7420):417-421 (published online Sep. 10, 2012).*
Bonsignori, M., et al., Oct. 2011, Analysis of a clonal lineage of HIV-1 envelope V2/V3 conformational epitope-specific broadly neutralizing antibodies and their inferred unmutated common ancestors, J. Virol. 85(19):9998-10009 (published online Jul. 27, 2011).*
Alam, S. M., et al., Feb. 2013, Antigenicity and immunogenicity of RV144 vaccine AIDSVAX clade E envelope immunogen is enhanced by a gp120 N-terminal deletion, J. Virol. 87(3):1554-1568.*
Li, Y., et al., 1994, Control of expression, glycosylation, and secretion of HIV-1 gp120 by homologous and heterologous signal sequences, Virol. 204:266-278.*
Land A., and I. Braakman, 2001, Folding of the human immunodeficiency virus type 1 envelope glycoprotein in the endoplasmic reticulum, Biochimie 83:783-790.*
Ellerbrok, H., et al., Aug. 1992, Functional tolerance of the human immunodeficiency virus type 1 envelope signal peptide to mutations in the amino-terminal and hydrophobic regions, J. Virol. 66(8):5114-5118.*
Alam et al "Antigenicity and immunogenicity of RV144 vaccine AIDSVAX clade E envelope immunogen is enhanced by a gp120 N-terminal deletion" J Virol. Feb. 2013;87(3):1554-68.
Doria-Rose et al "A Short Segment of the HIV-1 gp120 V1/V2 Region is a Major Determinant of Resistance to V1/V2 Neutralizing Antibodies" J Virol. Aug. 2012; 86(15): 8319-8323.

EPO Search Report dated Aug. 24, 2016.

Esparza et al "The Global HIV/AIDS Vaccine Enterprise: Scientific Strategic Plan" PLoS Medicine; Feb. 2005; 2(2) 0111-0121.

Haynes et al "Immune-correlates analysis of an HIV-1 vaccine efficacy trial" N Engl J Med. Apr. 5, 2012; 366(14):1275-1286.

Karasavvas et al "The Thai Phase III HIV Type 1 Vaccine trial (RV144) regimen induces antibodies that target conserved regions within the V2 loop of gp120" AIDS Res Hum Retroviruses. Nov. 2012;28(11):1444-57.

(Continued)

*Primary Examiner* — Jeffrey S Parkin

(74) *Attorney, Agent, or Firm* — Baker Donelson

(57) ABSTRACT

The present invention relates, in general, to human immunodeficiency virus-1 (HIV-1) particular, to a polyvalent vaccine for HIV-1 and to methods of making and using same.

12 Claims, 22 Drawing Sheets

Specification includes a Sequence Listing.

(56) References Cited

OTHER PUBLICATIONS

Keele et al "Identification and characterization of transmitted and early founder virus envelopes in primary HIV-1 infection" Proc Natl Acad Sci U S A. May 27, 2008;105(21):7552-7.

Liao et al "Antigenicity and immunogenicity of transmitted/founder, consensus, and chronic envelope glycoproteins of human immunodeficiency virus type 1" J Virol. Apr. 2013;87(8):4185-201. doi: 10.1128/JVI.02297-12.

Liao et al "Vaccine induction of antibodies against a structurally heterogenous site of immune pressure within HIV-1 envelope protein variable region 1 and 2" Immunity. Jan. 24, 2013;38(1):176-86.

McLellan et al "Structure of HIV-1 gp120 V1/V2 domain with broadly neutralizing antibody PG9" Nature. Nov. 23, 2011; 480(7377): 336-343.

Pinter et al "Potent neutralization of primary HIV-1 isolates by antibodies directed against epitopes present in the V1/V2 domain of HIV-1 gp120" Vaccine; Nov. 1998;16(19):1803-11.

Plotkin et al "Nomenclature for immune correlates of protection after vaccination" Clin Infect Dis. Jun. 2012;54(11)1615-7.

Rerks-Ngarm et al "Vaccination with ALVAC and AIDSVAX to prevent HIV-1 infection in Thailand" N. Eng. J. Med.; 2009; 361:2209-20.

Rolland et al "Genetic impact of vaccination on breakthrough HIV-1 sequences from the STEP trial" Nat Med. Mar. 2011;17(3):366-71.

Rolland et al "Increased HIV-1 vaccine efficacy against viruses with genetic signatures in Env V2" Nature Oct. 18, 2012;490(7420):417-20.

Zolla-Pazner et al "Structure-function relationships of HIV-1 envelope sequence-variable regions refocus vaccine design" Nat Rev Immunol. Jul. 2010;10(7):527-35.

International Preliminary Report on Patentability and Written Opinion of the ISA, PCT/US2014/034126, dated Oct. 20, 2015.

International Search Report, PCT/US2014/034126, dated Aug. 1, 2014.

Klausner et al "Medicine. The need for a global HIV vaccine enterprise" Science; Jun. 27, 2003;300(5628):2036-9.

Jolla-Pazner et al, AIDS Vaccine, Bangkok, Thailand, Abstract No. OA09.03,77 (2011).

Bradley, Todd, et al. "Pentavalent HIV-1 vaccine protects against simian-human immunodeficiency virus challenge" Nature Communications | 8:15711 | DOI: 10.1038/ncomms15711http://www.nature.com/naturecommunications; publised Jun. 8, 2017.

Human immunodeficiency virus type 1 (HIV-1) envelope glycoprotein, GenBank Accession No. AFU29418, Version AFU29418.1, published Feb. 10, 2017.

Human immunodeficiency virus type 1 (HIV-1) envelope glycoprotein, GenBank Accession No. AFU32681, Version AFU32681.1, published Feb. 10, 2017.

Human immunodeficiency virus typw 1 (HIV-1) envelope glycoprotein, GenBank Accession No. AFU32849, Version AFU32849.1, published Feb. 10, 2017.

Li, Yan, et al. "Control of expression, glycosylation, and secretion of HIV-1 gp120 by homologous and heterologous signal sequences." Virology 204.1 (1994): 266-278.

Li, Yan, et al. "Effects of inefficient cleavage of the signal sequence of HIV-1 gp 120 on its association with calnexin, folding, and intracellular transport." Proceedings of the National Academy of Sciences 93.18 (1996): 9606-9611.

Li, Yan, et al. "The HIV-1 Env protein signal sequence retards its cleavage and down-regulates the glycoprotein folding." Virology 272.2 (2000): 417-428.

Checkley, Mary Ann, Benjamin G. Luttge, and Eric O. Freed. "HIV-1 envelope glycoprotein biosynthesis, trafficking, and incorporation." Journal of molecular biology 410.4 (2011): 582-608.

Moody, M. Anthony, et al. "TLR-7/8 and 9 agonists cooperate to enhance HIV-1 envelope antibody responses in rhesus macaques." Journal of virology (2014): vol. 88, No. 6, Mar. 15, 2014, pp. 3329-3339.

* cited by examiner

FIGURE 1
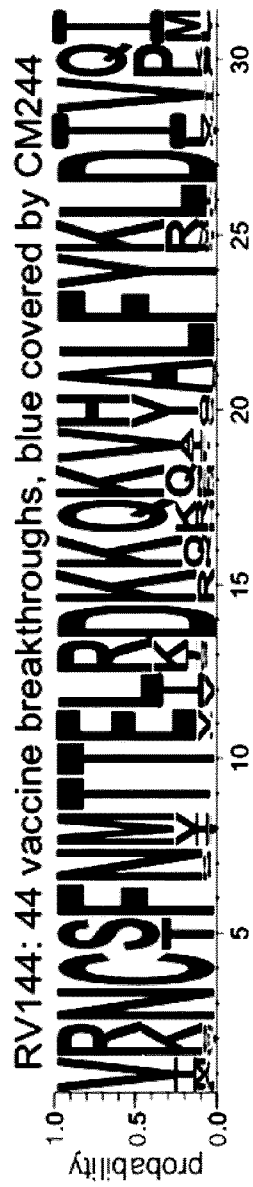
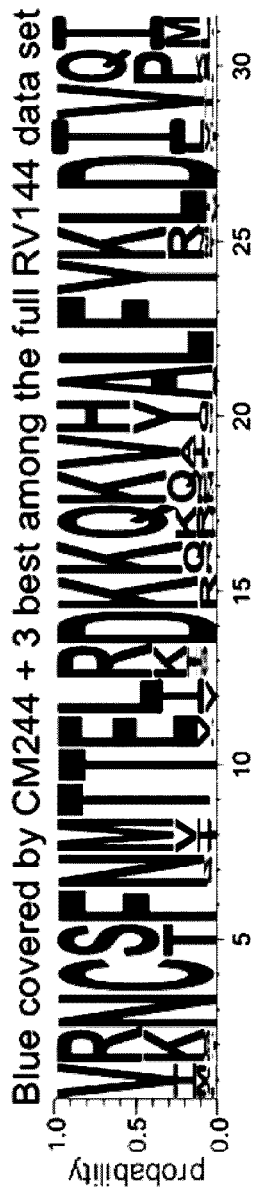
Optimal set to cover the RV144 data set, selected from among the breakthroughs and the placebo-recipient infected individuals:
```

FIGURE 5

```
ENV_92TH023_VCP1521         VRNCSFNMTTELRDKKQKVHALFYKLDIVPI
ENV_CM244                   -------------------------------
RV144.CONSENSUS.0           ---------------------Y--------Q-
RV144.CONSENSUS.1           ------------------------------Q-
ENV_CON_01_AE               ------------------------------Q-
ENV_HXB2_K03455             IK-----IS-SI-G-V--EY-F------I--
ENV_MN_DD328842             MK-----I--SI---M--EY--L-------A-

Bes4NaPlaVac.Seq35.CM244    -------------------------------
Bes4NaPlaVac.Seq97.AA104.0  ----T------I------AY-------L-QL
Bes4NaPlaVac.Seq107.0       -K--T--V----K------Y---------QM
Bes4NaPlaVac.Seq16.AA058.1  -K--T---------Q--------R----Q-

Bes4NaVac.Seq35.CM244       -------------------------------
Bes4NaVac.Seq24.AA072.1     ----T------I-------Q----R------
Bes4NaVac.Seq2.AA009.1      -K----KI-------Q---Y---------QM
Bes4NaVac.Seq5.AA015.1      -K--T-------K---K------------Q-

CON_AA006.1                 IK---------I---Q---Y------V---SM
CON_AA009.1                 -K----KI-------Q---Y---------QM
CON_AA012.1                 -Q--T-----VVS-R--Q-S----R---TQ-
CON_AA013.1                 -T---------T--RRM------R------
CON_AA015.1                 -K--T-------K---K------------Q-
CON_AA018.1                 ----T--T---------Q-Y---------Q-
CON_AA021.1                 ----T------I---QH-----------QM
CON_AA024.1                 A------V-------V-E-Y---------Q-
CON_AA028.1                 I---T-------K---------------QM
CON_AA034.1                 AK------A-----------Q----------
CON_AA036.1                 -------------------FY---------S-
CON_AA048.1                 MK---------K------------E----Q-
CON_AA050.1                 ----------VI-----Q-------------
CON_AA052.1                 IS--T------I----K--------N----K-
CON_AA055.1                 ----T--V----------------RI-----
CON_AA058.1                 -K--T---------Q--------R----Q-
CON_AA061.1                 ------------------------------M
CON_AA062.1                 I------V----K-----TY--------L-Q-
CON_AA063.1                 -K---------V------------------Q-
CON_AA064.1                 -K----K---V----R-Q----------V---
CON_AA065.1                 I----------K-R----Y-----P----L
CON_AA066.1                 ----------I-K----Q-------------
CON_AA070.1                 -K--T------I---E-QI----------Q-
CON_AA072.1                 ----T------I-------Q----R------
CON_AA073.1                 -K--T---S-------H--Y----------L
CON_AA074.1                 -T--T---P--IK-R--QIS----------NS
CON_AA077.1                 LK-----T---------Q------------Q-
CON_AA080.1                 I---T------I---QH------------E-
CON_AA085.1                 -K-----I---IK-R-K--------R----QL
CON_AA089.1                 I---T------VT----------------M
CON_AA090.1                 -K----------Q-NFY----R----Q-
CON_AA092.1                 I------I---II---KQ-Y--------T-Q-
CON_AA097.1                 -----------------QIY-----------
CON_AA100.1                 --------I-------QR--Q----R---IQT
CON_AA103.1                 -------------------------------
CON_AA108.1                 -K-----T----------AY---------QM
CON_AA111.1                 -K----DV--D-K--T--D---------K-
CON_AA113.1                 ------------N----NI---------IQ-
CON_AA118.1                 --------I-------QR--Q----R---IQT
CON_AA121.1                 ----T--V---I----KN-Y--------L-QM
CON_AA123.1                 ------------------Y------------
```

FIGURE 5 Cont.

```
CON_AA125.1         --------I---II-----R-Q-------------
CON_AA127.1         MK--------------------------QM
CON_AA131.1         -K---------I--RQ--------------L
CON_AA001.0         ----T-----VVS------Y-------L--M
CON_AA002.0         I--------------R-T-Y-------V---
CON_AA003.0         -K----------II-----FY--------IQ-
CON_AA004.0         -K----------IH-R---------------
CON_AA005.0         -K-----V--------QKQI------M----S-
CON_AA007.0         -K--T------T---K-AYS---R------
CON_AA008.0         IK--T-----D-K---R-------T----Q-
CON_AA014.0         --------I---------RAY----------
CON_AA016.0         ---------------K------------M----Q-
CON_AA017.0         ------------I-------------R------
CON_AA019.0         I---T------I-----ETY-----------
CON_AA022.0         -K--T------VQ----E-------E----Q-
CON_AA023.0         -K-----I-----------AY----S------
CON_AA026.0         ----------V---QR---Y---------Q-
CON_AA027.0         ----------IQ------Y---------Q-
CON_AA029.0         MK---------K------Y----T----QM
CON_AA030.0         ------------E---RR------R--L-K-
CON_AA031.0         --------------------------R--L-QM
CON_AA032.0         -K----K-----K---K--Y---------QM
CON_AA033.0         -K--------L-T------------R------
CON_AA035.0         ---------------HQ-Y----------
CON_AA037.0         IS----R-------------------N----K-
CON_AA038.0         -K--T---------------------R----QL
CON_AA041.0         SM--T------IK---T--N---------QM
CON_AA042.0         --------------------Y---------Q-
CON_AA044.0         -S--T-S-----A-R----Y----------V
CON_AA045.0         -------I---I-----KQ-Q---------QM
CON_AA049.0         -----------I-----------------Q-
CON_AA051.0         -K---------T-----AYS---R----S-
CON_AA054.0         -K--T-----------Q-R-------V--M
CON_AA056.0         ------S----I-------Y-----I-T-S-
CON_AA057.0         -----------I---Q--L----------Q-
CON_AA059.0         I---T---------R-KQ-Y----------
CON_AA060.0         M-------IK-TK-R----Y-T---------
CON_AA067.0         -K---------VT---KQ------R----QM
CON_AA068.0         ----T--V----K----Q-Y-----P-----
CON_AA069.0         -K----I-----------AY----M------
CON_AA075.0         -M--T----------KQ-Q-------M-QM
CON_AA076.0         ----T----------R-------------IQ-
CON_AA078.0         -KV-A--V---IK---R-------------L
CON_AA079.0         -Q--T--V----I--Q---R-------L-Q-
CON_AA081.0         M---------------Q-Y-----------
CON_AA082.0         -K--T-----------R------R--L-QM
CON_AA083.0         -------V--V-Q-----------R--L-Q-
CON_AA086.0         ----------VI---Q-QI-----------
CON_AA088.0         M--------------QK-------R--LA--
CON_AA091.0         I-----------K------Y-------V-Q-
CON_AA094.0         -----------IK----------------
CON_AA098.0         -----------I-----RIY----------
CON_AA099.0         -------SV----K-----------R----QM
CON_AA101.0         L-----------------------RV-MI--
```

FIGURE 5 Cont.

```
CON_AA102.0          ----------VV-------Y-----------
CON_AA104.0          ----T------I------AY-------L-QL
CON_AA105.0          AK--T----------Q---Y----N----Q-
CON_AA106.0          -K--T-------T------------------
CON_AA107.0          -K--T--V----K------Y---------QM
CON_AA109.0          -K-----V---I--R---AY-------L-QM
CON_AA110.0          -K--T------------GY--------Q-
CON_AA112.0          ----T--T----K---K-----------KM
CON_AA116.0          L------V------RQR-AY-----------
CON_AA117.0          --------------R----Y-----I-L-Q-
CON_AA119.0          ------------G----Q-Y-F--N--L-Q-
CON_AA122.0          MK-----V--VI-----Q----------RM
CON_AA126.0          I---T------I-----M-----------EM
CON_AA129.0          -K-----T--------K-SY-----------
CON_AA130.0          -K---Y-----IK-------S---R------
```

FIGURE 6

```
The more complete Envs:
CON_AA104.0t
MRVKETQMIWPNLWKWGTLILGLVIICSASDNLWVTVYYGVPVWRDADTTLFCASDAKA
HGTEVHNIWATHACVPTDPNPQEIHLANVTENFNMWKNNMVEQMQEDIISLWDQSLKPC
VQLTPLCVTLNCAIANLTNANANLT-----------
NINLNITGNITDEVRNCTFNMTTEIRDKKQKAYALFYKLDLVQLKD-------------
--------
SNDSNRYMLINCNTSVIKQACPKISFDPIPIHYCAPAGYAILKCNDKNFNGTGPCRNVS
SVQCTHGIKPVVSTQLLLNGSLAEEEIIIRSENLTNNAKTIIVHLNKSVEINCTRPSNN
TRTSISIGPGQ-VFYKTGDIIGDIKKAYCEINATKWNETLKQVIGKLKEHFN----
NKTIIF--QPPSGGDLEITTHHFNCRGEFFYCNTSRLFKNET---------------
EEVNGTIILPCRIKQIINMWQGVGQAMYAPPIRGRINCISNITGILLTRDGG-------
---------
KNASNETFRPGGGNIKDNWRSELYKYKVVQIEPLGIAPSRARRRVVEREKRAVGIGAMI
FGFLGAAGSTMGAASITLTVQARQLLSGIVQQQSNLLRAIEAQQHLLQLTVWGIKQLQA
RVLAVERYLKDQQLLGLWGCSGKTICTTAVPWNSTWSNKSYDEIWGNMTWVQWEREISN
YTNQIYEVLMESQNQQDRNEKDLLELDKWASLWNWFDITRWLWYIKIFIMIVGGLIGLR
IIFAVLSIVNRVRQGYSPLSLQIPTHQQREPDRLERIEEGGGEQDRDRSVRLVSGFFAL
AWDDLRSLCLFSYHLLRDFILIVTRTVV-------
KGLRRGWEGLKYLGNLLLYWGQELKISAISLLNATAIRVGGWTDRVIEVAQGAWRAVLH
IPRRIRQGFERALL CON_AA107.0t
MRVKETQMNWPNWWKGVTLILGLVIICRASDNLWVTVYYGVPVWRDAETTLFCASDAKA
HDTEVHNVWATHACVPTDPNPQELYLENVTENFNMWTNKMVEQMHEDVISLWDQSLKPC
IKLTPLCVTLNCTNAMFNNTNANSTASV------
TTDDGTNRIGNLTDEVKNCTFNVTTELKDKKQKVYALFYKLDIVQMPN-----------
--------------
SEYRLINCNTSVIKQACPKITFDPIPIHYCTPAGYAILKCNDKNFNGTGPCKNVSSVQC
THGIKPVVSTQLLLNGSLAEEEIIIRSENLTNNAKTIIVHFNKSVEINCTRPSNNTRTS
VHIGPGQ-VFYRTGDIIGDIRKAYCEVNGTRWNKVLKQVTNKLKEKFH----HKTIKF-
-QPPSGGDLEITMLHFNCRGEFFYCNTTSLFNDTCIGN----------
ETKEGCNTTIILPCRIKQIVNMWQGVGQAMYAPPISGRINCVSNITGILLTRDGG----
-----------
VNNDSSEIFRPGGGDIRDKWRSELYKYKVVQIEPLGVAPTRAKRRVVERPKRAVGIGAM
IFGFLGAAGSTMGAASITLTVQARQLLSGIVQQQSNLLRAIEAQHHLLQLTVWGIKQLQ
ARVLAVERYLKDQKFLGLWGCSGKVICTTAVPWNSTWSNKSYDEIWNNMTWIEWEREIG
NYTSQIYEILTESQNQQDRNEKDLLALDHWASLWNWFDITKWLWYIKIFIMIVGGLIGL
RIVFAVLSIVNRVRQGYSPVSFQIPTHQQREPDRPERIEEGGGEQDRDRSVRLVTGFLA
LLWDDLRSLCLFSYHRLRDLLLIAKRTVELLGYSSLKGLRRGWEILKYLGNLLLYWGRE
LKISAVSLFDAIAIAVAGWTDRVIEVVQRAWRAILHIPRRIRQGLERALL CON_AA058.1t
MRVKGTQMNWPNLWRWGTLILGLVIICSASNNLWVTVYYGVPVWKDADTTLFCASDAKA
HETEVHNVWATHACVPTDPNPQEIHLENVTENFNMWKNNMVEQMQEDVISLWDQSLKPC
```

FIGURE 6 Cont.

```
VKLTPLCVTLNCTEAKLSQTANNQTG----------
NITDGGDIGKITEEVKNCTFNMTTELRDKQQKVHALFYRLDIVQINSN-----------
--------
DNNSREYRLINCNTSVIKQACPKVSFDPIPIHYCTPAGYAILKCNDKKFNGTGPCKNVS
SVQCTHGIKPVVSTQLLLNGSLAEEDIIIRSENLTNNAKNIIVQFNKSVEINCTRPSNN
TRTSVSIGPGQ-VFYKTGDIIGDIRKAYCEINGTKWNETLKQVVGKLREYF-----
NKTIIF--RPPSGGDLEITTHYFNCRGEFFYCNTTKLFNSTWTEN----------
GTEERFNDTIILPCKIKQIVNMWQRAGQAMYNPPIKGKINCVSNITGIILIRDGG----
----------
ANNTNNNETFRPGGGNIKDNWRSELYKYKVVQIEPLGIAPTRAKRRVVEREKRAVGIGA
MIFGFLGAAGSTMGAASITLTVQARQLLSGIVQQQSNLLRAIEAQQHLLQLTVWGIKQL
QARVLAVERYLKDQKFLALWGCSGKIICTTTVPWNSTWSNKSYEDIWNNMTWTQWEREI
SNYTNQIYEILTESQTQQDKNEKDLLAMDKWATLWNWFDITKWLWYIRIFIIIVGGLIG
LRIIFAVLSIVNRVRQGYSPLSFQIPSHHQREPDRPEGTEEGGGEQGRDKSIRLVSGFL
AVFWDDLRSLCLFSYHLLRDFSLIAARTVELL-------
LRRGWEGLKYLGNLLIYWGQELKISAISLLDTIAIAVAGWTDRIIEAAQRAGRAILHIP
RRIRQGLERLLL
```

FIGURE 7

RV144: 44 vaccine breakthroughs, blue covered by CM244

Blue covered by CM244 + 3 best among the full RV144 data set

Optimal set to cover the RV144 data set, selected from among the breakthroughs and the placebo-recipient infected individuals:

```
                 156   160            169    181
                                169-171 173
Vaccine  VRNCSFNMTTELRDKKQKVHALFYKLDIVPI
AA104.0       T                 I     AY           L
AA107.0  K    T      V          K     Y            L
AA058.1  K    T                  Q    R            M
```

Vaccine = CM244/92TH023, highly similar sequences, and identical in this region.
156 & 160: McLellan, key glycosyaltion sites for PG9 and similar bNabs
169 & 181: Rolland signature
169-171 & 173: Doria-Rose, 169-171 positive charge, and 173Y increased PG9 sensitivity

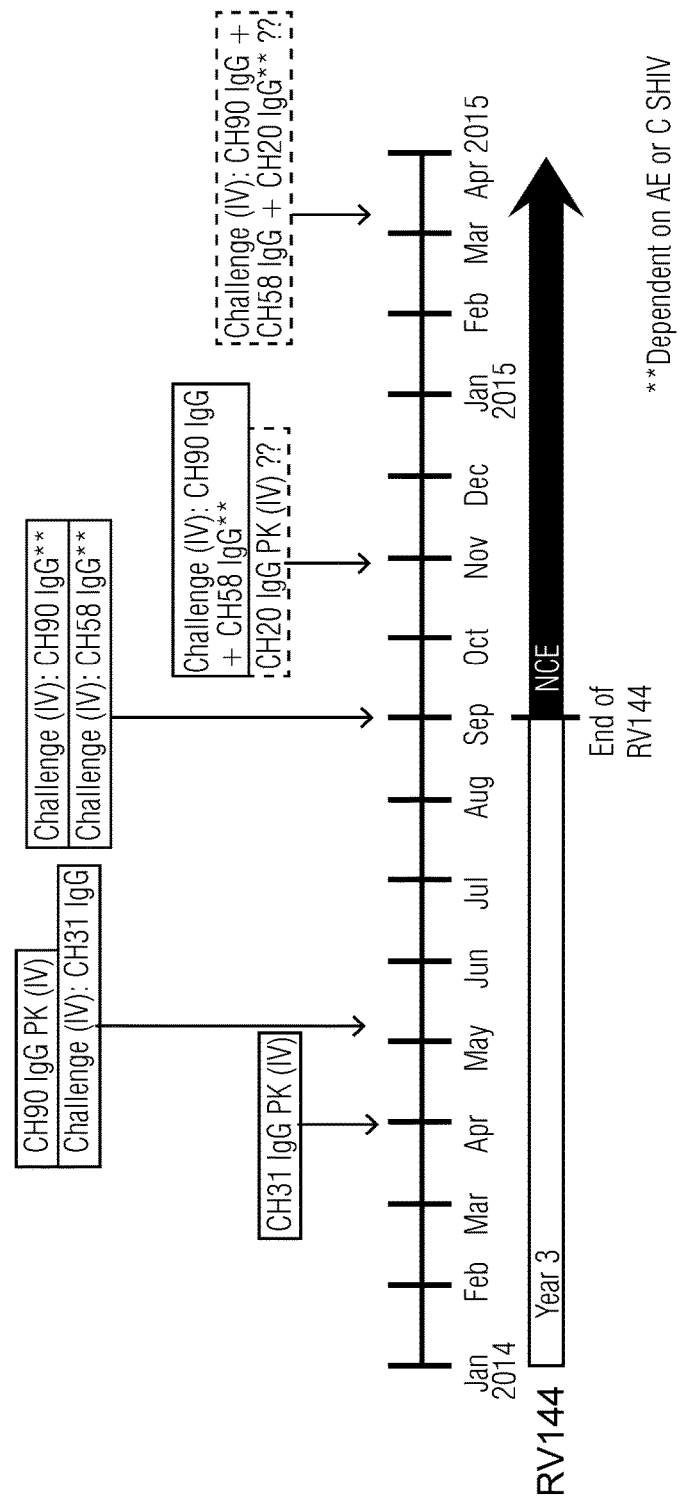

METHODS OF INDUCING AN IMMUNE RESPONSE AGAINST HIV-1 USING RECOMBINANT ENVELOPES WITH IMPROVED COVERAGE

This application claims the benefit of U.S. Provisional Application Ser. No. 61/812,093 filed Apr. 15, 2013, the entire content of which application is herein incorporated by reference.

GOVERNMENT INTERESTS

The invention was made with government support under grant W81XWH-07-2-0067 awarded by the United States Army Medical Research and Materiel Command and Contract No. DE-AC52-06NA25396 awarded by the U.S. Department of Energy. The government has certain rights in the invention.

SEQUENCE LISTING

The instant application contains a Sequence Listing which has been submitted electronically in ASCII format and is hereby incorporated by reference in its entirety. Said ASCII copy, created on Nov. 18, 2015, is named 2933311-014.US2_SL.txt and is 69,118 bytes in size.

TECHNICAL FIELD

The present invention relates, in general, to human immunodeficiency virus-1 (HIV-1) and, in particular, to a polyvalent vaccine for HIV-1 and to methods of making and using same

BACKGROUND

Development of a safe, practical and effective HIV-1 vaccine is one of the highest priorities of the global scientific community (Klausner et al, Science 5628:2036-2039 (2003); Esparza et al, Science Strategic Plan, DOI: 10.1371/journal.pmec10020025, Policy Forum Vol. 2, February 2005). While anti-retroviral treatment (ART) has dramatically prolonged the lives of HIV-1 infected patients, anti-retroviral therapy is not yet routinely available in developing countries, and the global rate of spread of HIV-1 continues at unacceptably high levels.

A recent efficacy trial the RV 144 vaccine demonstrated an estimated 31.2% vaccine efficacy (Rerks-Ngarm et al, N. Eng. J. Med. 361: 2209-20 (2009). The RV144 vaccine is comprised of the following: ALVAC-HIV (vCP1521) is a recombinant canarypox vaccine developed by Virogenetics Corporation (Troy, N.Y.) and manufactured by Sanofi Pasteur (Marcy-l'Etoille, France). The recombinant canarypox was genetically engineered to express HIV-1 Gag and Pro (subtype B LAI strain) and CRF01_AE (subtype E) HIV-I gp120 (92TH023) linked to the transmembrane anchoring portion of gp41 (LAI), AL V AC Placebo (Sanofi Pasteur) was a sterile, lyophilized product consisting of virus stabilizer and freeze-drying medium reconstituted in 1 ml of 0.4% sodium chloride.

AIDSV AX B/E (Global Solutions for Infectious Diseases, South San Francisco, Calif.) is a bivalent HIV gp120 envelope glycoprotein vaccine containing a subtype E envelope from the HIV-1 strain A244 (CM244) and a subtype B envelope from the HIV-1 MN produced in Chinese hamster ovary cells. The envelope glycoproteins, 300 μg of each, originally manufactured by Genentech, Inc., and further developed by VaxGen, Inc., are co-formulated with 600 μg of alum adjuvant. AIDSVAX placebo (VaxGen, Inc.) was 600 μg alum adjuvant. The RV144 vaccine was administered as two primes with ALVAC-HIV (vPC 1521) followed by two boosts with a combination of ALV AC-HIV and AIDSV AX B/E (Rerks-Ngarm et al, N. Eng. J. Med. 361: 2209-20 (2009).

In 2012 an immune correlates study of the RV 144 trial revealed that antibodies against the envelope (Env) gp120 V1/V2 region presented on a gp70-15 VI/V2 fusion protein (Pinter et al, Vaccine 16:1803 (1998) were associated with lower risk of infection (Haynes et al., New Engl. J. Med. 366:1275-1286 (2012). Epitope mapping of plasma VI IV2 antibody responses showed that within V2, vaccine-induced antibodies targeted a region of HIV-1 Env, amino acid (aa) residues at positions 163-178 (Liao et al, Immunity 38: 1 76 (2013); Karasavvas et al, AIDS Research and Human Retroviruses, doi: 10.1089/aid.20 12.0103 (2012), Zolla-Pazner et al, AIDS Vaccine, Bangkok, Thailand Abstract No.: OA09.03, 77 (2011). There is considerable sequence variability in V1V2, ~75% of the residues are conserved or demonstrated to be only conservative changes (ZollaPazner & Cardozo, Nat Rev Immunol 10,527-535 (2010). While the demonstration that of V1V2 antibody responses directly correlated with decreased infection risk was suggestive of their protective role in the trial, this association was not sufficient for proving causation of protection (Plotkin & Gilbert, Clinical infectious diseases: an official publication of the Infectious Diseases Society of America 54: 1615-1617 doi: 10,1093/cid/cis238 (2012). Indeed further studies are needed to evaluate the ability of such responses to mediate immune pressure on HIV-1, Viral genetic (sieve) analyses, isolation of VI IV2 antibodies and understanding their effector function in vitro and in vivo, and validation of correlates of infection risk in future vaccine trials are some potential studies.

A genetic or sieve analysis of sequences of viruses that caused breakthrough infections in a vaccine trial can demonstrate vaccine effects (Rolland et al, Nature Medicine 17:366-371 (2011). By comparing sequences of breakthrough infections that occur in vaccinees versus placebo recipients, sites of vaccine-induced immune pressure can be identified (Rolland et al, Nature Medicine 17:366-371 (2011). A recent genetic analysis of breakthrough HIV-1 infections in the RVI44 trial demonstrated 48% (CI: 18 to 68%, p=O,0036) vaccine efficacy against viruses matching the CRF_01 AE vaccine immunogens with a lysine (K) at position 169 (Rolland et al, Nature 490:417-420 (2012). Thus, it is critical to determine the binding site and effector functions of RV 144-induced V1/V2 antibodies. Effector functions considered for antibody mediated protection from HIV-1 transmission include the ability of V1/V2 antibodies to neutralize those virus strains involved in HIY-1 transmission (i.e. transmitted/founder viruses) (Keele et al, Proc Natl Acad Sci USA 105:7552-7557 (2008), and/or to mediate other antibody effector functions such as antibody-dependent cellular cytotoxicity (ADCC) (Haynes et al, New Engl. J. Med, 366:1275-1286 (2012).

The present invention results, at least in part, from studies designed to identify an envelope(s) (Env(s)) that can be used in combination with the original RV144 vaccine ((Rerks-Ngarm et al, N, Eng, J. Med. 361: 2209-20 (2009)) to improve the coverage by a new vaccine formulation of the epitope diversity in the V2 region in the Thai population. The present invention provides, at least in part, new vaccine immunogens that induce high titers of V1V2 (and other CRF_01AE gp120 regions) vaccine responses to HIV-1 envelope gp120.

SUMMARY OF THE INVENTION

In certain aspects the invention provides a composition comprising an HIV-1 envelope AA104.0 (FIG. 6, SEQ ID NO: 1), AA107.0 (FIG. 6, SEQ ID NO: 2), AA058.1 (FIG. 6, SEQ ID NO: 3), or a combination thereof. In certain embodiments, the composition comprises AA104.0 (SEQ ID NO: 1), AA107.0 (SEQ ID NO: 2) and AA058.1 (SEQ ID NO: 3). In certain embodiments, the envelope is a gp120Delta N-terminus polypeptide from SEQ ID NOs: 1, 2 or 3 (See paragraph [0038] infra). In certain embodiment, the gp120Delta N-terminus polypeptide is gp120 delta12 based on SEQ ID NOs: 1, 2, and 3. In certain embodiments the compositions of the invention further comprises HIV-1 envelopes used in the RV144 trial, or modified versions thereof, for example but not limited to gp120delta N terminus polypeptides. In certain embodiments, the composition comprise envelopes B.6240 gp120D11, Env B. 63521 delta 11 gp120, A244 gp120 D11, or a combination thereof.

In certain embodiments the envelopes are recombinant proteins.

In certain aspects, the invention provides compositions comprising a nucleic acid encoding any one of the envelopes described herein. In certain embodiments, the nucleic acids are optimized for expression in any suitable expression system.

In certain embodiments, the compositions of the invention further comprise an adjuvant. In certain embodiments the adjuvant is Toll-like receptor 4 agonist glucopyranosyl lipid adjuvant (GLA). In certain embodiments, the adjuvant is a Toll-like receptor 4 agonist glucopyranosyl lipid adjuvant-stable emulsion (GLA/SE). In certain embodiments the compositions of the invention is immunogenic.

In certain aspects, the invention provides methods of inducing and/or boosting an immune response in a subject comprising administering to the subject any one of the inventive compositions. In certain embodiments, the composition is administered as a boost. In certain embodiments, the compositions are administered as multiple boosts.

In certain aspects the invention provides an immunogen comprising AA104.0, AA107.0, AA058.1, AA072.1, AA009.1, or AA015.1 envelope. In certain aspects the invention provides a method of inducing an immune response in a subject comprising administering to the subject an amount of the immunogen described here sufficient to effect the induction. In certain embodiments of the inventive methods of the subject is a human.

The present invention relates generally to HIV-1. More specifically, the invention relates to a polyvalent vaccine for HIV•1 and to methods of making and using same. Objects and advantages of the present invention will be clear from the description that follows.

BRIEF DESCRIPTION OF THE DRAWINGS

FIG. 1. AA 1 04 provides the best complementary coverage used in conjunction with A244, for covering the full RV144 data set. The coverage is indicated in blue for A244 at the top, and the improved coverage by using 3 at the bottom. Figure discloses SEQ ID NOS 4 and 11-13, respectively, in order of appearance.

FIG. 5. An alignment of the V2 region, HXB2 positions 154-184, of RV144 placebo (0.0) and vaccine (0.1) sequences, best coverage sequences, relative to A244. Figure discloses SEQ ID NOS 15-139, respectively, in order of appearance.

FIG. 6. Full sequences of candidate vaccines. In one embodiment, a gp120Delta N-terminus polypeptide design includes a deletion of the amino acids tween the signal peptide (ending with CS in AA104.0 and AA058.1 and ending with CR in AA107.0) and the sequence "VPV". Figure discloses SEQ ID NOS 1-3, respectively, in order of appearance.

FIG. 7 shows new AE Envs to be added to RV144 B/E boost. Figure discloses SEQ ID NOS 4 and 11-13, respectively, in order of appearance.

FIG. 17 shows Planned Passive Protection Challenges.

DETAILED DESCRIPTION OF THE INVENTION

Figure 2:
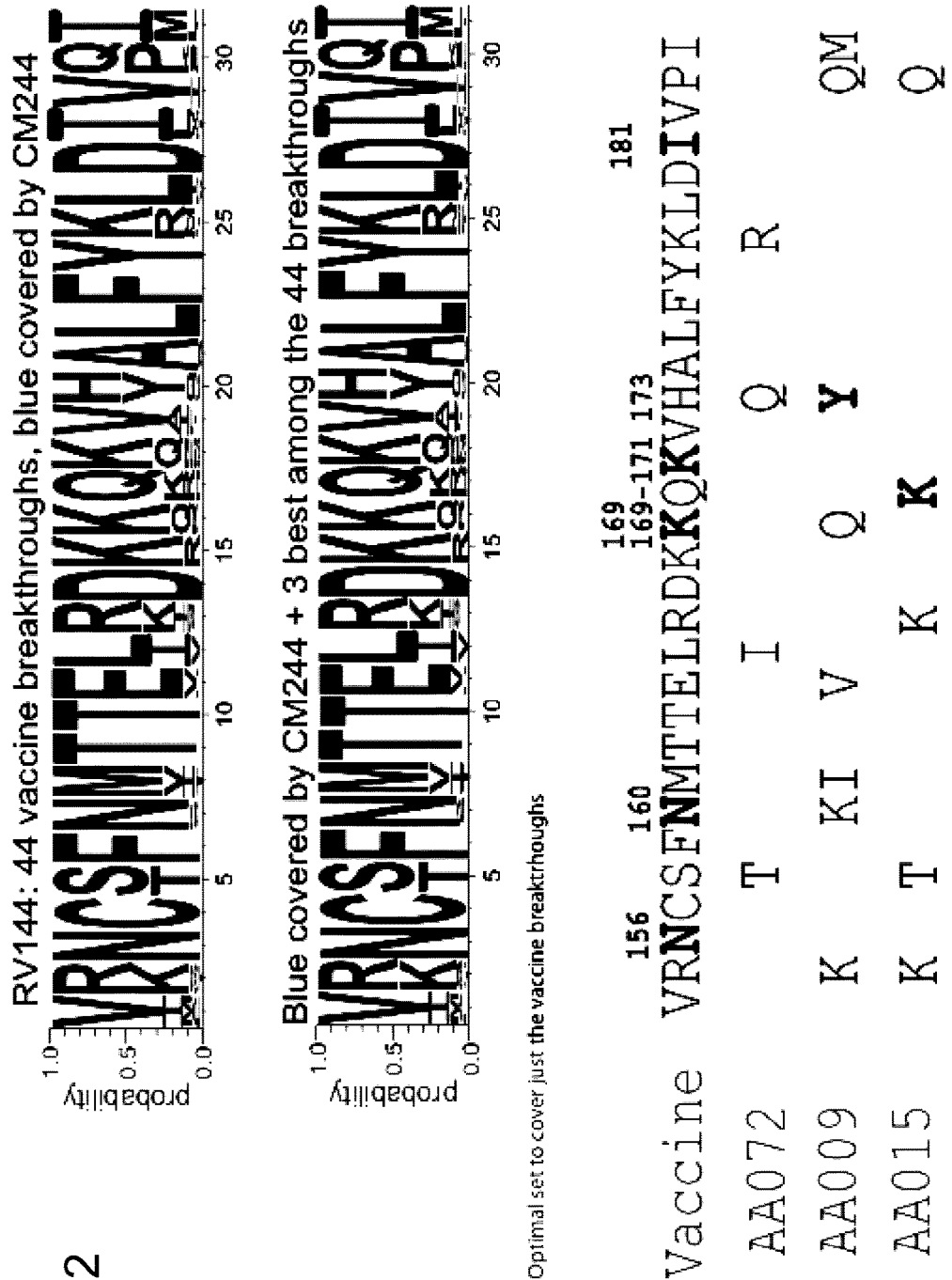
FIG. 2. Second vaccine selection, based on RV 144 vaccine breakthrough cases. Figure discloses SEQ ID NOS 4 and 8, 14, and 10, respectively, in order of appearance.

The RV 144 vaccine is described in detail above, as is the administration regimen. (See also Rerks-Ngarm et al, N. Eng. J. Med. 361: 2209-20 (2009).) The present invention results, at least in part, from studies designed to identify an envelope(s) (Env(s)) that can be used in combination with the original RV 144 vaccine to improve the coverage by a new vaccine formulation of the epitope diversity in the V2 region in the Thai population.

An approach taken in accordance with the present invention is to substitute the A244 gp120 Delta11 Env (Alam et al, J. Virol. 87:1554 (2013) incorporated by reference) for the A244 gD+gp120 that was used in RV144 and to substitute for the MN gp120 in AIDSVAX B/E, the transmitted founder Env B. 63521 delta 1 gp120 ((Alam et al, J. Virol. 87:1554-68 (2013), e.g. Materials and Methods, incorporated by reference; Liao et al, J. Virol 87:4185 (2013) incorporated by reference), and then to the A244 gp120 delta 11 and B.63521 gp120 delta 11 Envs to add three additional Envs from CRF_01AE breakthrough infections in the RV144 trial.

In certain embodiments, a vaccine in accordance with the invention would have ALVAC-HIV vPC1521 prime X2 then ALVAX vPC1521 boost X2 with A244 gp 120 Delta 11+B.63521 Delta 11 gp120+AA104.0 delta11 or 7 gp120+AA107.0 delta11 or 7gp 120+AA058.1 delta 11 or 7 gp120. An alternate set of Envs is AA072.1, AA009.1, and AA015.1 from the list of Envs in the Example below.

Immunogens of the invention are suitable for use in generating an immune response in a patient (e.g., a human patient) to HIV. The mode of administration of the HIV-1 protein/polypeptide/peptide, or encoding sequence, can vary with the immunogen, the patient and the effect sought, similarly, the dose administered. Typically, the administration route will be intramuscular or subcutaneous injection (intravenous and intraperitoneal can also be used). Most advantageously, the route and interval of administration are the same as used in the original RV144 trial (Rerks-Ngarm et al, N. Eng. J. Med. 361: 2209-20 (2009). Optimum dosing regimens can be readily determined by one skilled in the art. The immunogens are preferred for use prophylactically, however, their administration to infected individuals may reduce viral load.

Certain aspects of the present invention are described in greater detail in the non-limiting Example that follows. (See also PCT/US2012/000570 and PCT/US20131029164.)

In certain embodiments, the envelope design in accordance with the present invention involves deletion of residues (e.g., 5-11, 5, 6, 7, 8, 9, 10, 11, 12, 13, 14, 15, 16, 17 amino acids) at the N-terminus. For delta N-terminal design, amino acid residues ranging from 4 residues or even fewer to 14 residues or even more are deleted. These residues are between the maturation (signal peptide, usually ending with CX, X can be any amino acid) and "VPVXXXX . . . ". In certain embodiments, the invention relates generally to an immunogen, gp160, gp120 or gp140, without an N-terminal Herpes Simplex gD tag substituted for amino acids of the N-terminus of gp120, with an HIV leader sequence (or other leader sequence), and without the original about 4 to about 25, for example 11, amino acids of the N-terminus of the envelope (e.g. gp120). See WO2013/006688, e.g. at pages 10-12, the contents of which publication is hereby incorporated by reference in its entirety. Various cell lines and methods for making recombinant proteins are known in the art.

The compositions can be formulated with appropriate carriers and adjuvants using techniques to yield compositions suitable for immunization. The compositions can include an adjuvant, such as, for example but not limited to, alum, poly IC, MF-59 or other squalene-based adjuvant, ASOIB, or other liposomal based adjuvant suitable for protein or nucleic acid immunization, GSK AS01E adjuvant containing MPL and QS21. This adjuvant has been shown by GSK to be as potent as the similar adjuvant AS01B but to be less reactogenic using HBsAg as vaccine antigen [Leroux-Roels et al., IABS Conference, Apr. 2013, 9]. In certain embodiments, TLR agonists are used as adjuvants. In other embodiment, adjuvants which break immune tolerance are included in the immunogenic compositions.

Dosing of proteins and nucleic acids can be readily determined by a skilled artisan. A single dose of nucleic acid can range from a few nanograms (ng) to a few micrograms (µg) or milligram of a single immunogenic nucleic acid. Recombinant protein dose can range from a few µg micrograms to a few hundred micrograms, or milligrams of a single immunogenic polypeptide. See also Rerks-Ngarm et al. NEJM 361: 2209-20 (2009) which content is herein incorporated by reference in its entirety.

Example 1

The study described below involves the selection of an Env or Envs that can be used in combination with the original RV144 vaccine to improve coverage of the epitope diversity in the V2 region in the Thai population. Selections were made from the RV144 vaccine breakthrough cases and also from the full RV144 set of breakthrough vaccinee and placebo HIV infections. The RV 144 placebos and the vaccinees were very similar as regards the frequencies of amino acids in the V2 region (and both were also highly similar to the database set of CRF01s; the degree of overlap even in the Rolland signature sites is quite high (Rolland et al, Nature 490:417-420 (2012). By using both the vaccine and placebo, rather than just vaccine, there are more sequences from which to select for optimization.

Consideration was given only the regions between the hypervariable loops in V1 and V2 (following McLellan et al, Nature 480:336~343 (2011) and Liao et al, Immunity 38: 176 (2013), HXB2 positions 154-184). It was possible to identify either the one best single complement to A244, or set of 3 that best complement A244 and cover the CRF_01AE virus diversity in Thailand. The region spans the PG9-like epitope region, as well as the region of the virus implicated in RV144 protection (Haynes et al, New Engl. J. Med. 366:1275-1286 (2012); Liao et al, Immunity 38: 176 (2013). The best natural strains for population coverage were selected, using the mosaic tool to select the natural strains, with a contiguous fragment length of 8. It was then confirmed that the selected Envs did not have long V1 and V2 hypervariable loops proximal to the V2 region, as the long loops may mask the epitopes in the region—the selected loops had modest loop lengths.

Use was made of the consensus sequence from each person to represent the population diversity of Envs; Rolland provided this set initially (Rolland et al, Nature 490:417-420 (2012) but a few subjects were remarkably diverse for early time point sequence sets, and so sometimes the Rolland set of by-subject-consensus sequences had frame shifts due to the alignment—these frameshifts are alignment artifacts that were not found among the natural strains. As a result, the original alignments were returned to and these issues addressed, to have intact Envs with viable loops to use for immunogen design. (The frameshift issue would not have impacted the Rolland signature analysis, as Rolland looked at a small set of sites that were translated correctly).

The two CFR01 vaccines used in RV144, A244 and 92TH023 (Rerks-Ngarm et al, N. Eng. J. Med. 361: 2209-20 (2009), are completely identical in the V2 region 154~184 and they are highly similar throughout Env, because they were both early isolates from Thailand epidemic, and so both are close to the ancestral state of the CRF01 founder in Thailand. With respect to V2, their shared sequence in this region happens to provide the best CRF01 population diversity coverage in VI V2 for a single sequence, because A244/92TH023 were both so close to the ancestral state, and so the shared sequence is central to modern strains. Although both of these early isolates are identical in the V2 region, the V2 region itself is highly diverse in Thailand and globally, which is to be expected, as this seems to be a good immune target so it is under immune pressure. RV144 used essentially the most central sequence possible in Thailand by using something very close to the ancestor.

A single vaccine strain that can be used to complement A244 (and 92TH023) in V2 is AA104.0 ("0.0" means it was from the placebo-infected group, "0.1" refers to the infected individuals who were vaccinated). Alternatively, AA104.0, AA107.0 and/or AA058.1 can be used with A244 and B.63521 Env gp120s.

The RV144 virus set was computationally analyzed and three Env sequences were chosen to be added to the B/E boost used in RV144 (See FIG. 1, 7.)

Example 3

NHP study (NHP #64) to compare bivalent (RV144) and pentavalent boost (9 rhesus macaques per group)

Group 4 (bivalent boost)—ALVAC vPC1521 prime ×2, then ALVAC VPC1521+B/E boost X2 (B.6240 gp120D11+ A244 gp120 D11 in GLA/SE)

```
                                                  Compared to:

RV144all  RVvac

Preferred is a vaccine based on all RV144:

ENV_CM244    VRNCTFNM|TTELRDKKQKVHALFYKLDIVPI
AA104.0      VRNCTFNMTTEIRDKKQKAYALFYKLDLVQL*         .32      .33
AA107.0      VKNCTFNVTTELKDKKQKVYALFYKLDIVQM
AA058.1      VKNCTFNMTTELRDKQQKVHALFYRLDIVQI          .44      .43

If a selection ism ade frmo only the vaccine breakthroughs, the
                         following are preferred:

ENV_CM244    VRNCSFNMTTELRDKKQKVHALFYKLDIVPI
AA072.1      VRNCTFNMTTEIRDKKQKVQALFYRLDIVPI*         .31      .34
AA009.1      VKNCSFKITTELRDKQQKVYALFYKLDIVQM
AA015.1      VKNCTFNMTTELKDKKKKVHALFYKLDIVQI          .41      .45
```

*(single best)

(SEQ ID NOS 4-10, Respectively, in Order of Appearance)

The coverage of ENV_CM244+AA 104.0 and ENV_CM244+AA072.1 are nearly comparable percent coverage if expressed as percent i.e., 0.31 is 31 percent. However, AA 104.0 may have additional advantages: it has the 173Y that increases a PG9 susceptibility (Doria-Rose et al, J. Virol. 86:8319-8323 (2012), and the set of 3 retains the sequence at 156 and 160 (McLellan et al, Nature 480:336-343 (2011). It also has the IL toggle at 181 (Rolland et al, Nature 490:417-420 (2012)).

The forgoing information is depicted in the Figures as follows:

FIG. 1. A LOGO plot of the variation in V2 in the RV144 whole set, with coverage indicated for A244, and then and compared to coverage provided by the best 3 complementary strains in the whole set from RV144.

FIG. 2. Same as above but using a set selected to cover the RV144 vaccine breakthrough group from RV 144.

Figure 3:
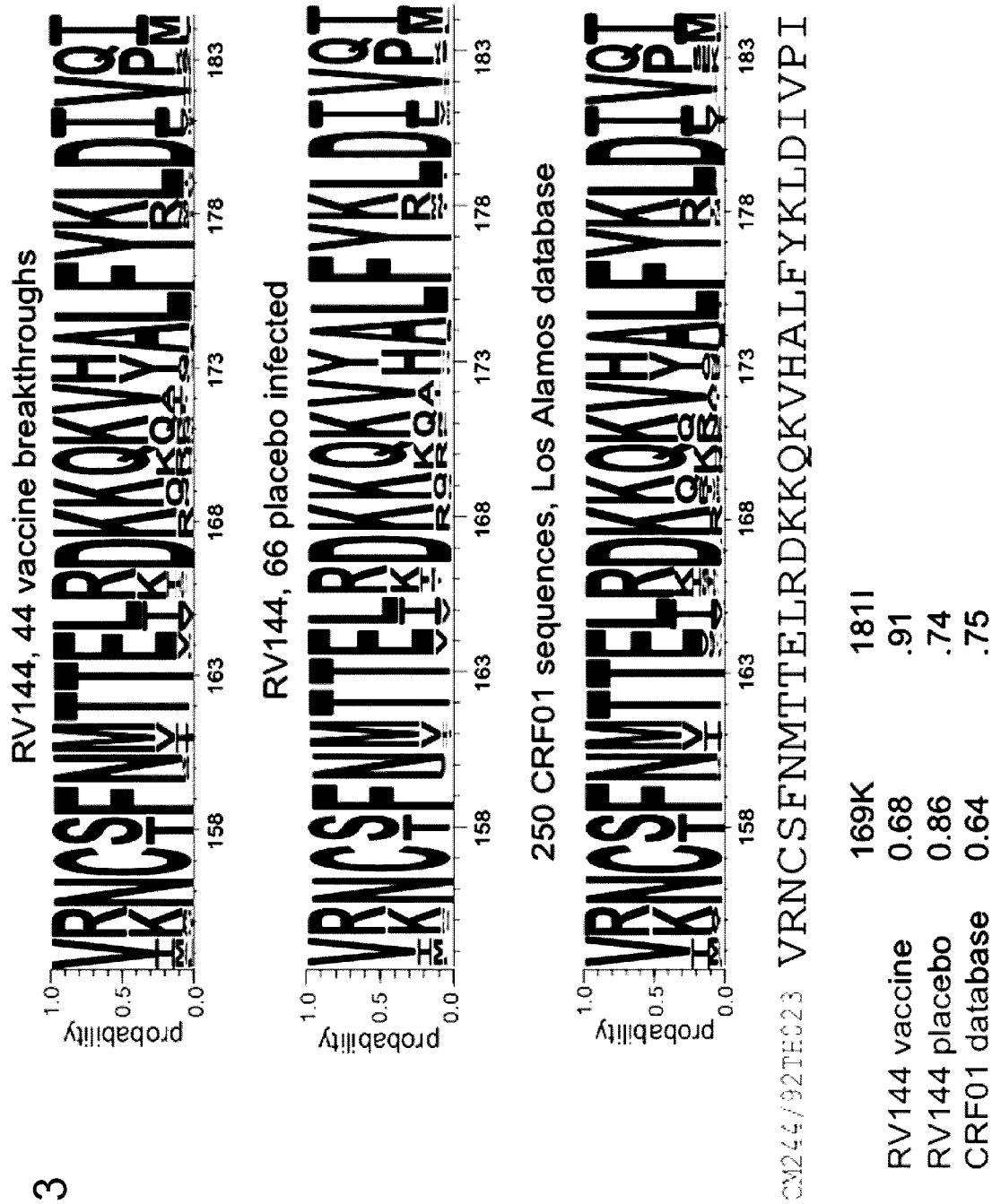
FIG. 3. Distribution of amino acids in CRF_01AE in the RV 144 trial in Thailand, compared with a global CRF_01 AE set in the Los Alamos HIV Sequence Database (at LANL.gov). Figure discloses SEQ ID NO: 4.

FIG. 3. Logos comparing the RV144 vaccine group, the RV144 placebo group and the database CRF01 cases, showing their similarity. The frequencies of the Rolland signatures at 169 and 181 are shown.

Figure 4:
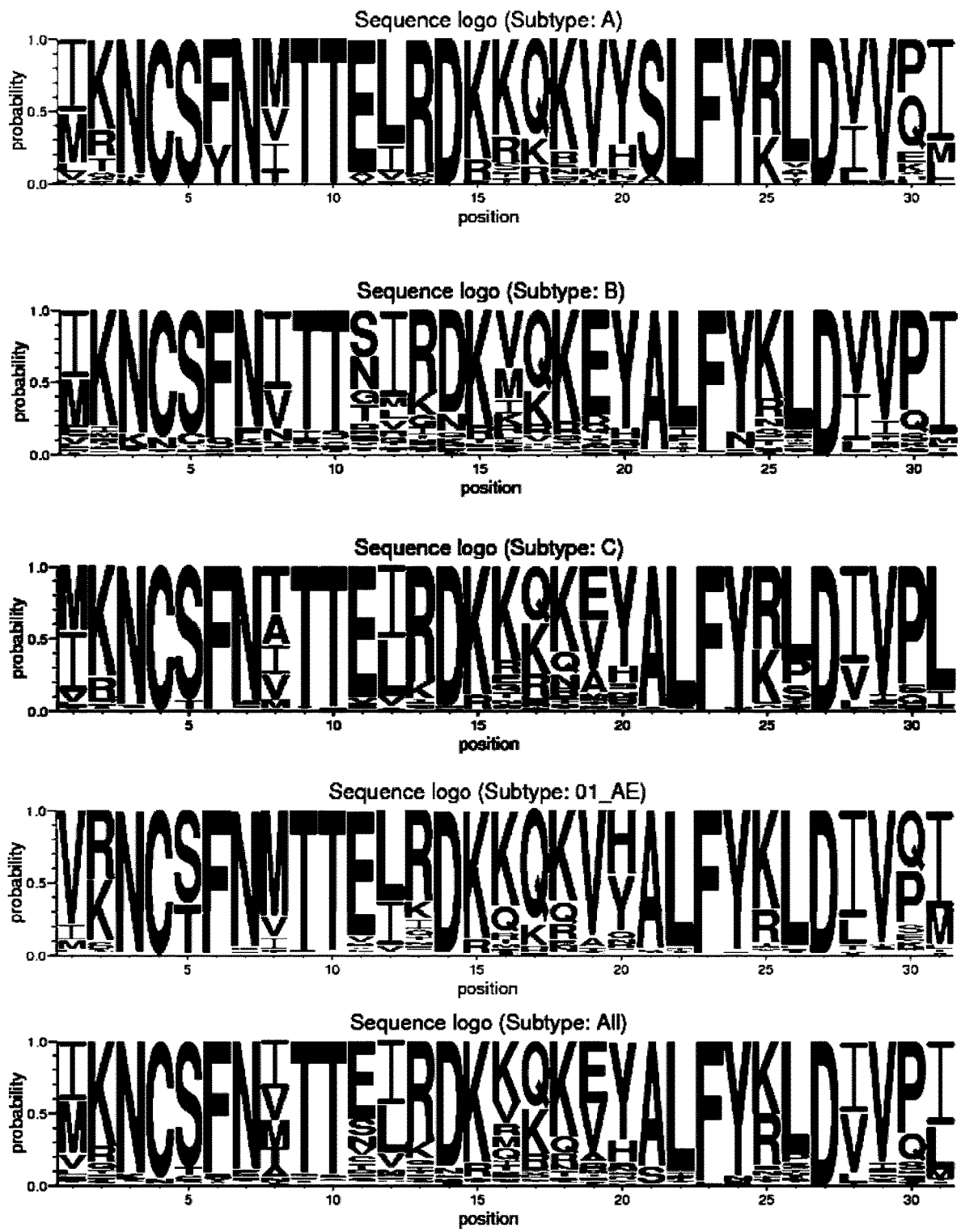
FIG. 4. Logos showing the subtype variation in this region in the HIV database. The glycosylation sites are well preserved but there are some differences in 169-173 and 181. Subtype B is not as positively charged in 169-171, and 173 Y most variable in CRF01. The glycosylation sites at 156 and 160 are preserved in all subtypes.
Figure 8A:
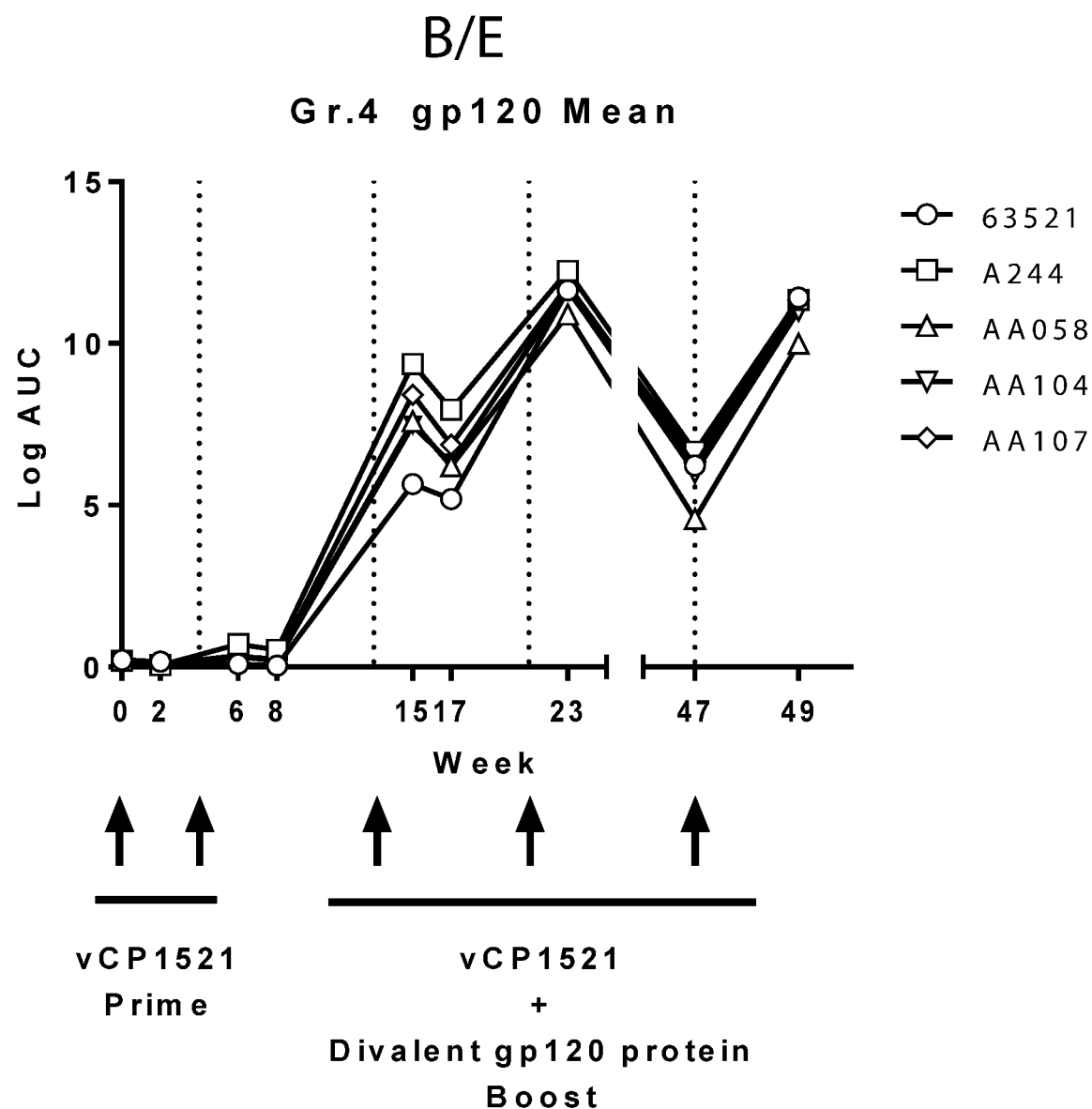
FIGS. 8A and 8B show Mean Plasma Binding to NHP #64 gp120 Immunogens by ELISA.
Figure 8B:
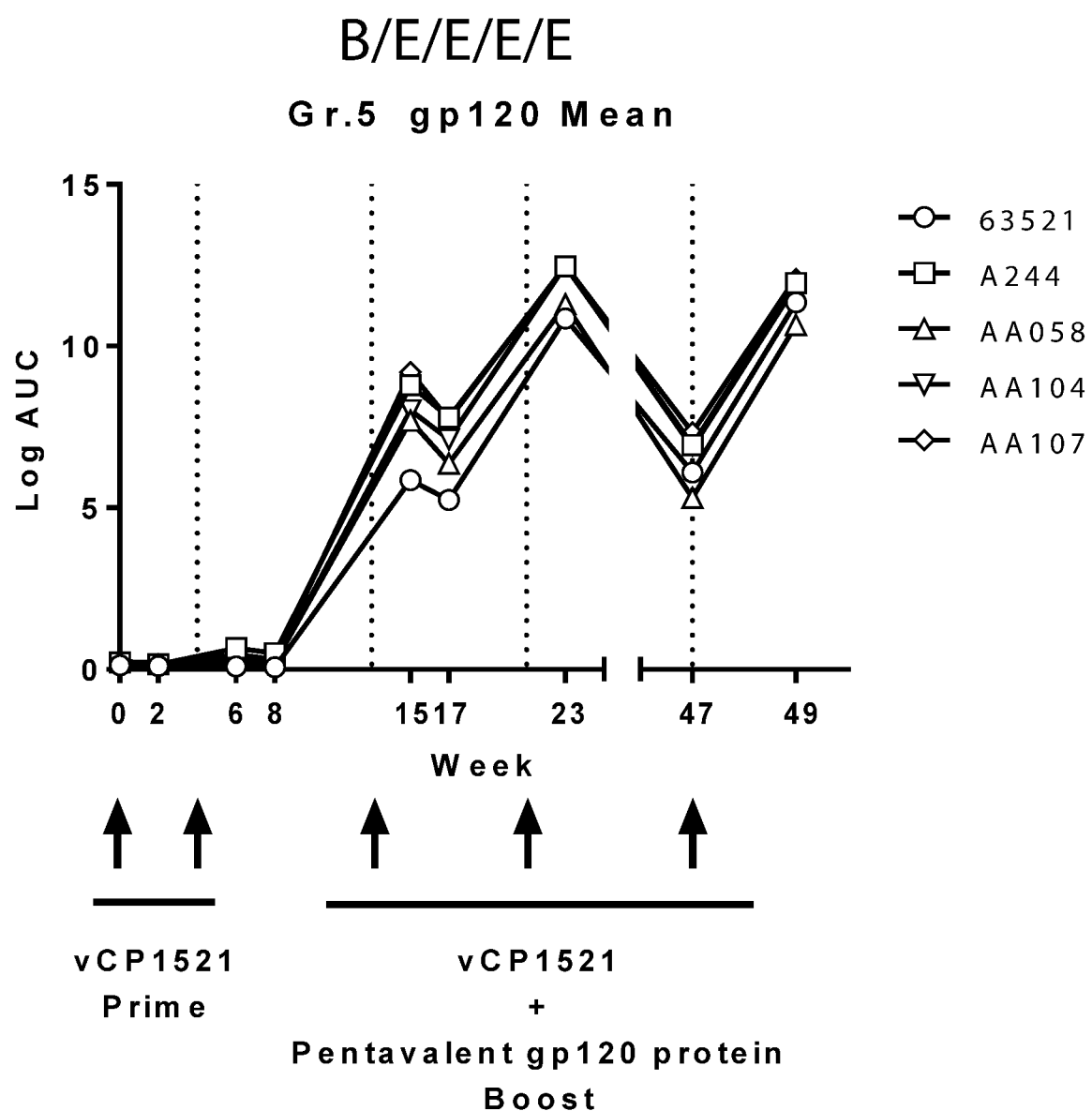
Figure 9:
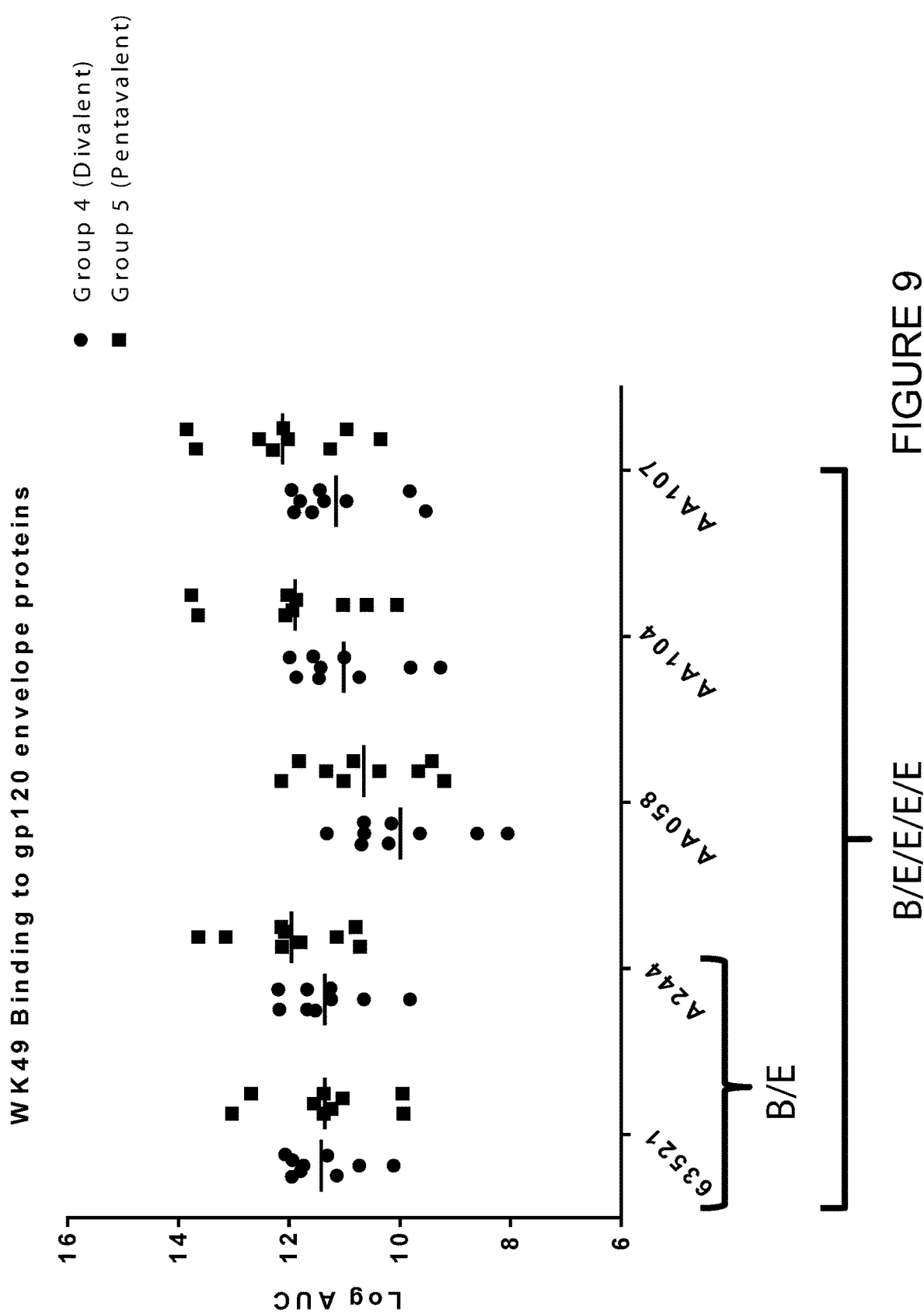
FIG. 9 shows Mean Plasma Binding to NHP #64 gp120 Immunogens by ELISA At Week 49 After 6 Months Rest
Figure 10A:
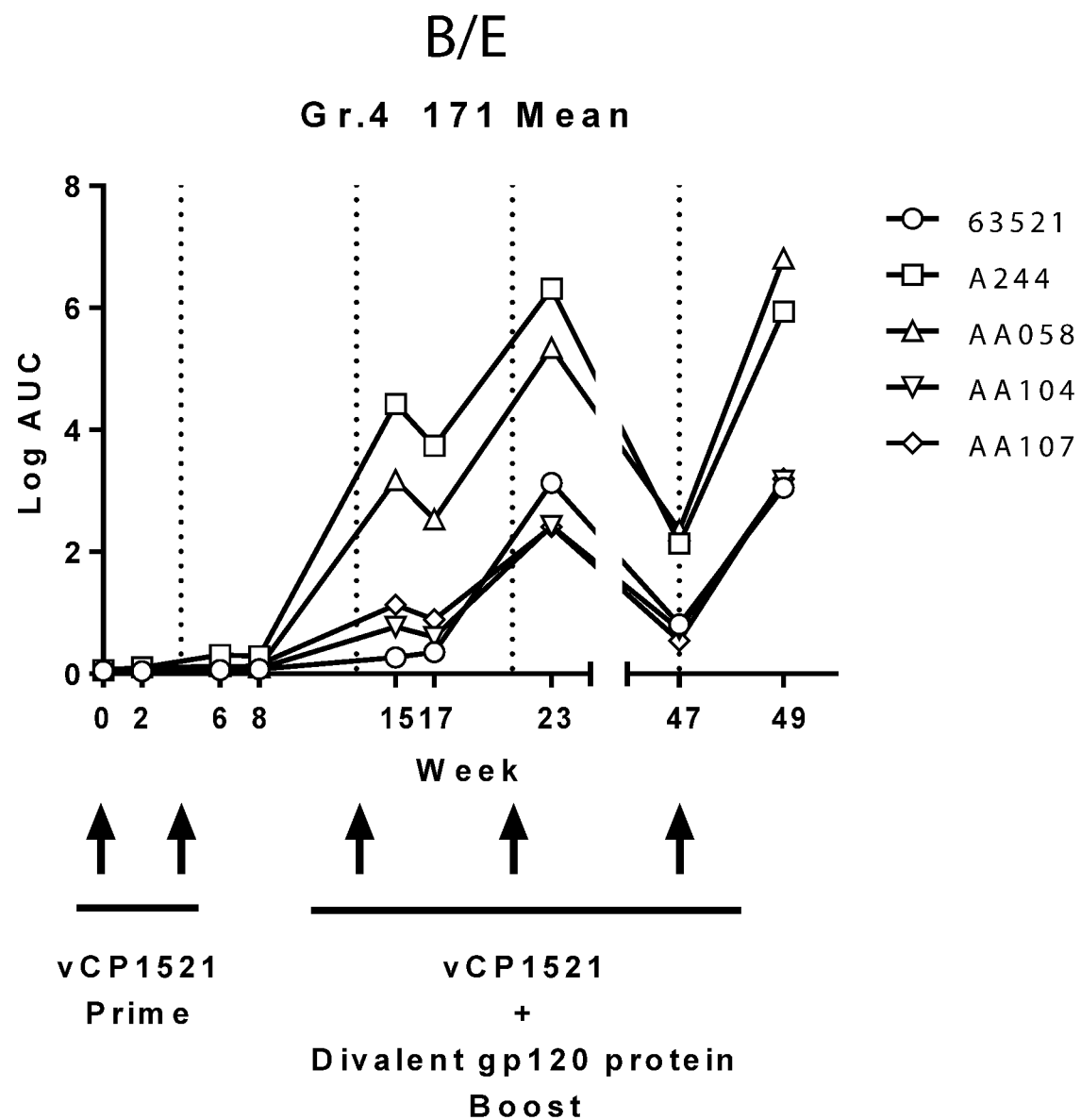
FIGS. 10A and 10B show Mean Plasma Binding to V2 171 Peptides by ELISA
Figure 10B:
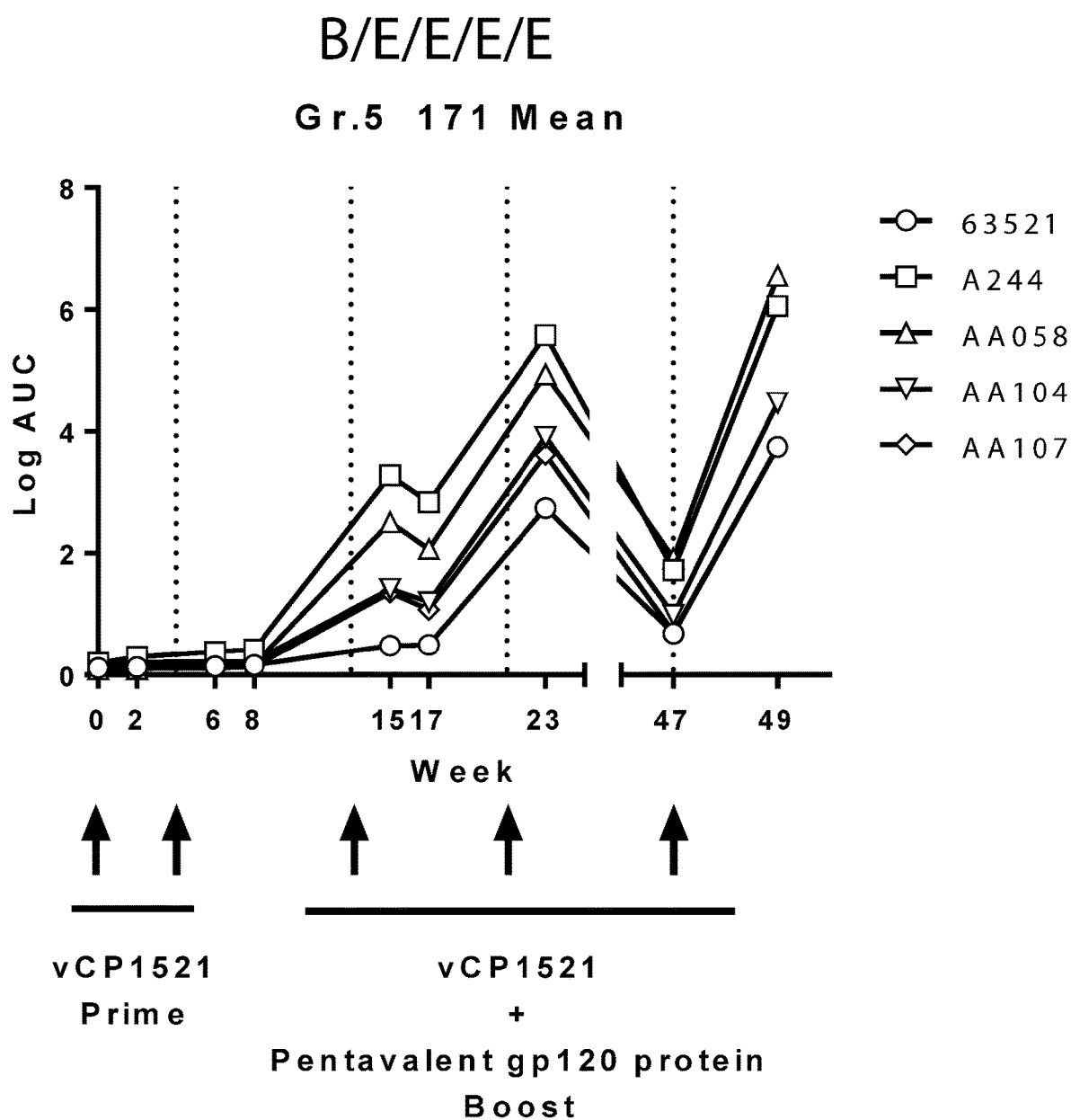
Figure 11:
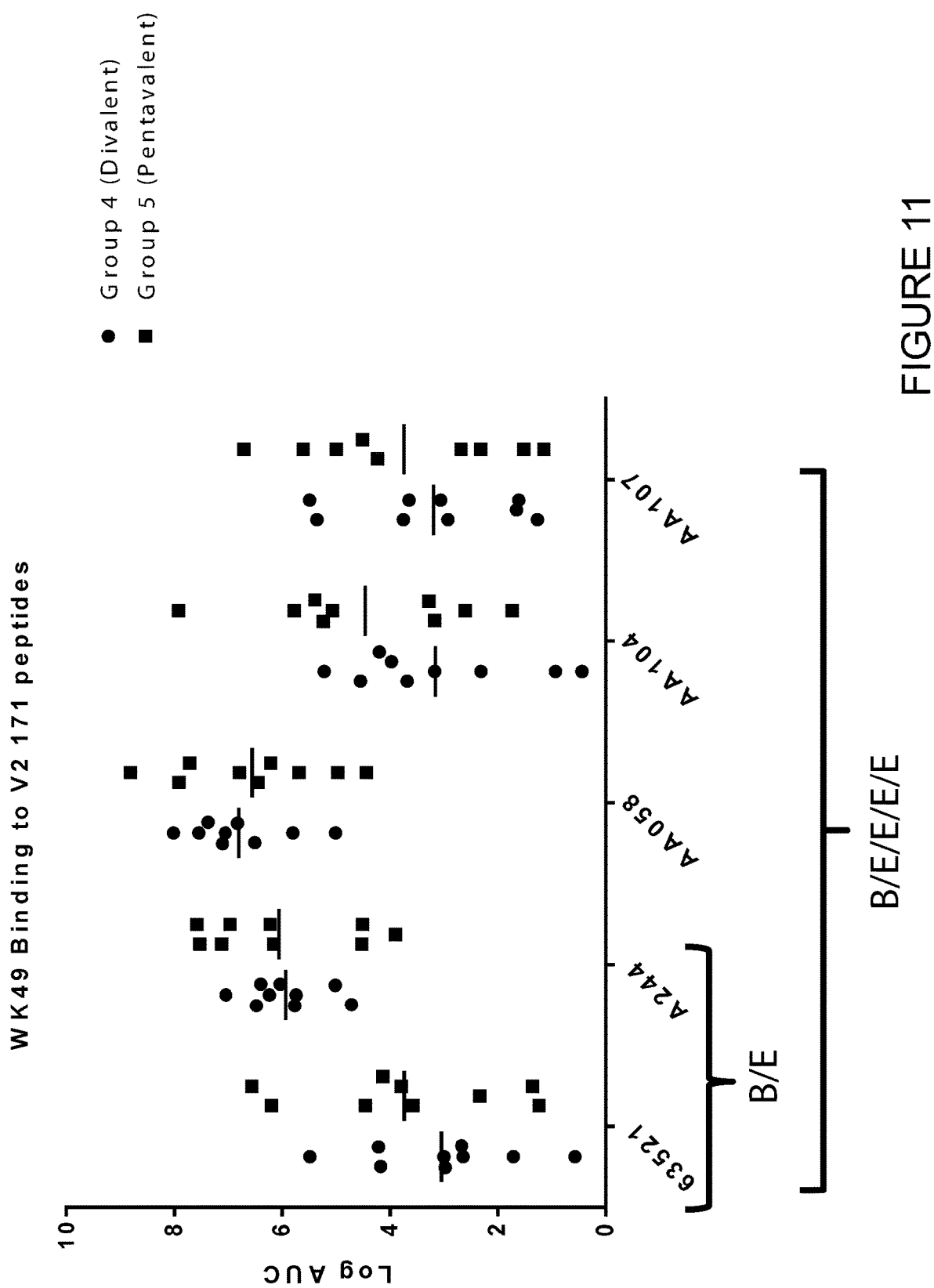
FIG. 11 shows Mean Plasma Binding to NHP #64 V2 Peptides by ELISA At Week 49 After 6 Months Rest

FIG. 4. LOGOS showing region diversity of clades A and G plots.

FIG. 5. An alignment of the V2 region, HXB2 positions 154-184, of RV144 placebo (0.0) and vaccine (0.1) sequences, best coverage sequences, relative to A244

FIG. 6. Full sequences of candidate vaccines.

Example 2

Improving the immunogenicity of "RV144" HIV-1 vaccine trial

Sieve analysis has shown that there is vaccine immune pressure at K169 in the HIV-1 envelopes. There is 48% vaccine efficacy if there is virus matched vaccine.

Group 5 (pentavalent boost)—ALVAC vPC1521 prime X2, then ALVAC VPC1521+B/E boost X2 (B.6240 gp120D11+A244 gp120 D11+new three valent AE gp120s in GLA/SE)

Both groups were boosted again after 6 months (February, 2014) and then will be boosted one more time (like RV305). The animals will be challenged with heterologous AE SHIV low dose rectal challenge—the AE SHIV could be either SHIV AE16 or SHIV 1157 tier 2 Y173H, and the challenge is planned for June, 2014.

FIGS. 8-11 show data from NHP #64 Group 4 (B/E) and Group 5 (B/E/E/E/) animals in plasma binding to gp120 Immunogens.

Figure 12:
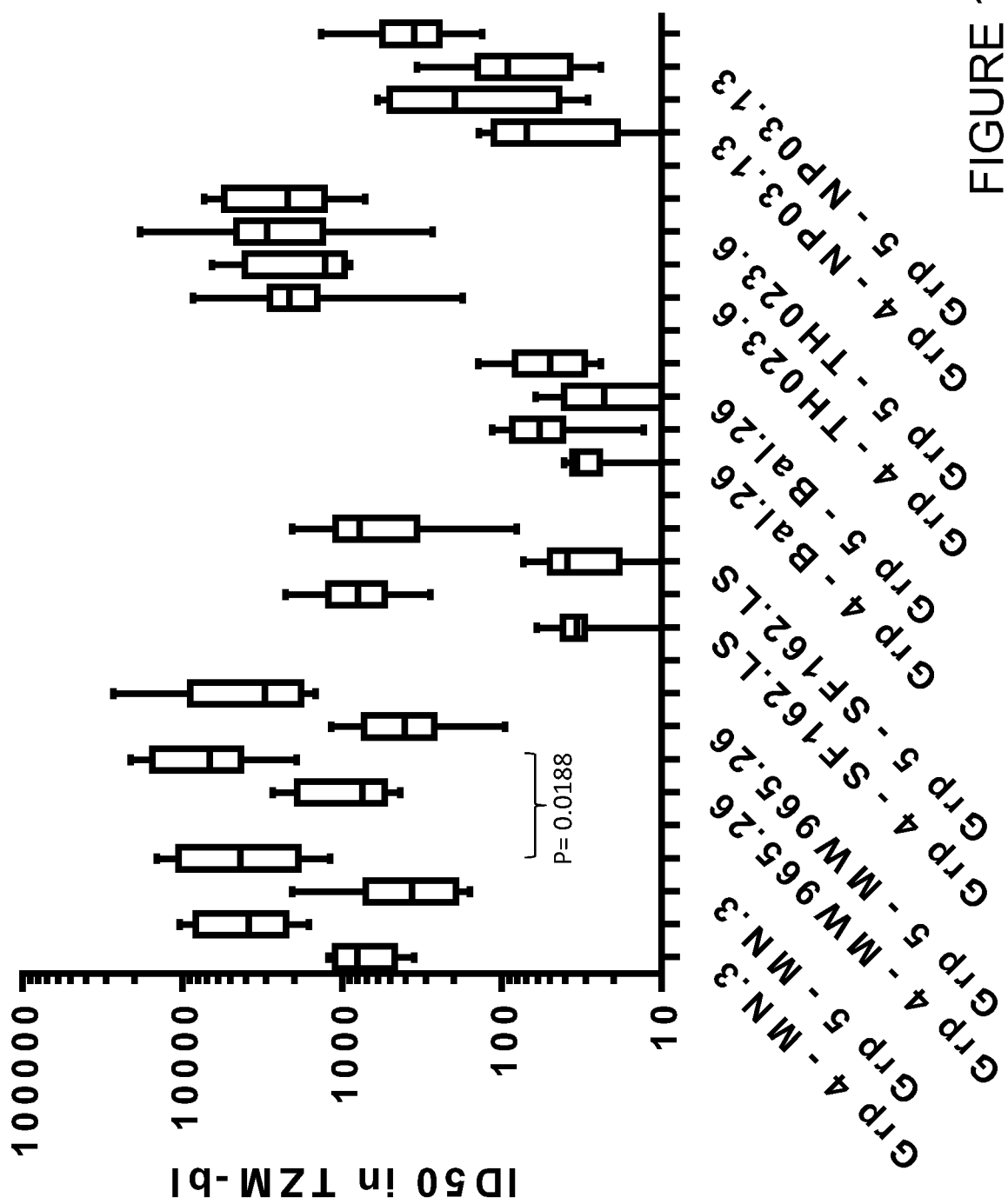
FIG. 12 shows Neutralization in the TZMbl Assay NHP #64—Week 23 (red), Week 49 (black)—group 4 (B/E) vs. group 5 (B/E/E/E)
Figure 13:
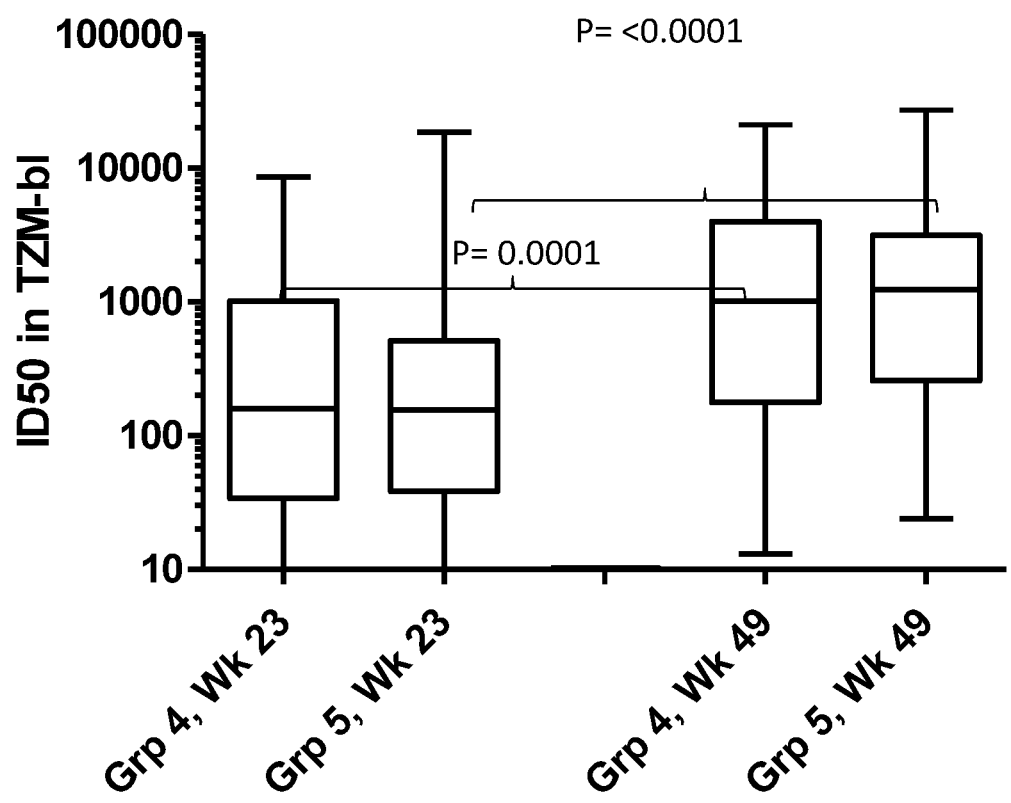
FIG. 13 shows NHP #64 TZM-bl, Aggregate Responses
Figure 14:
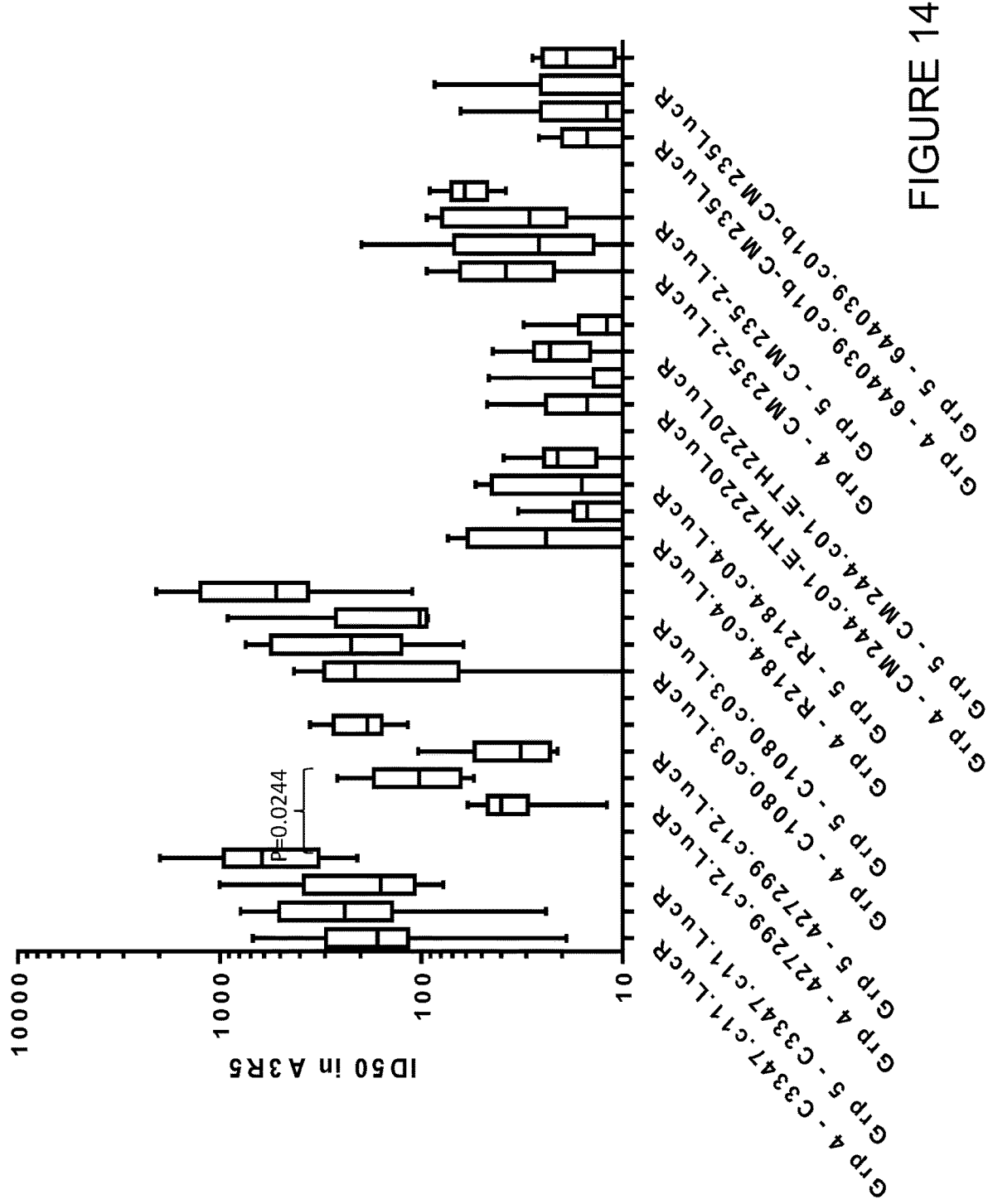
FIG. 14 shows Neutralization in the A3R5 Assay NHP #64—Week 23 (red), Week 49 (black)—group 4 (B/E) vs. group 5 (B/E/E/E)
Figure 15:
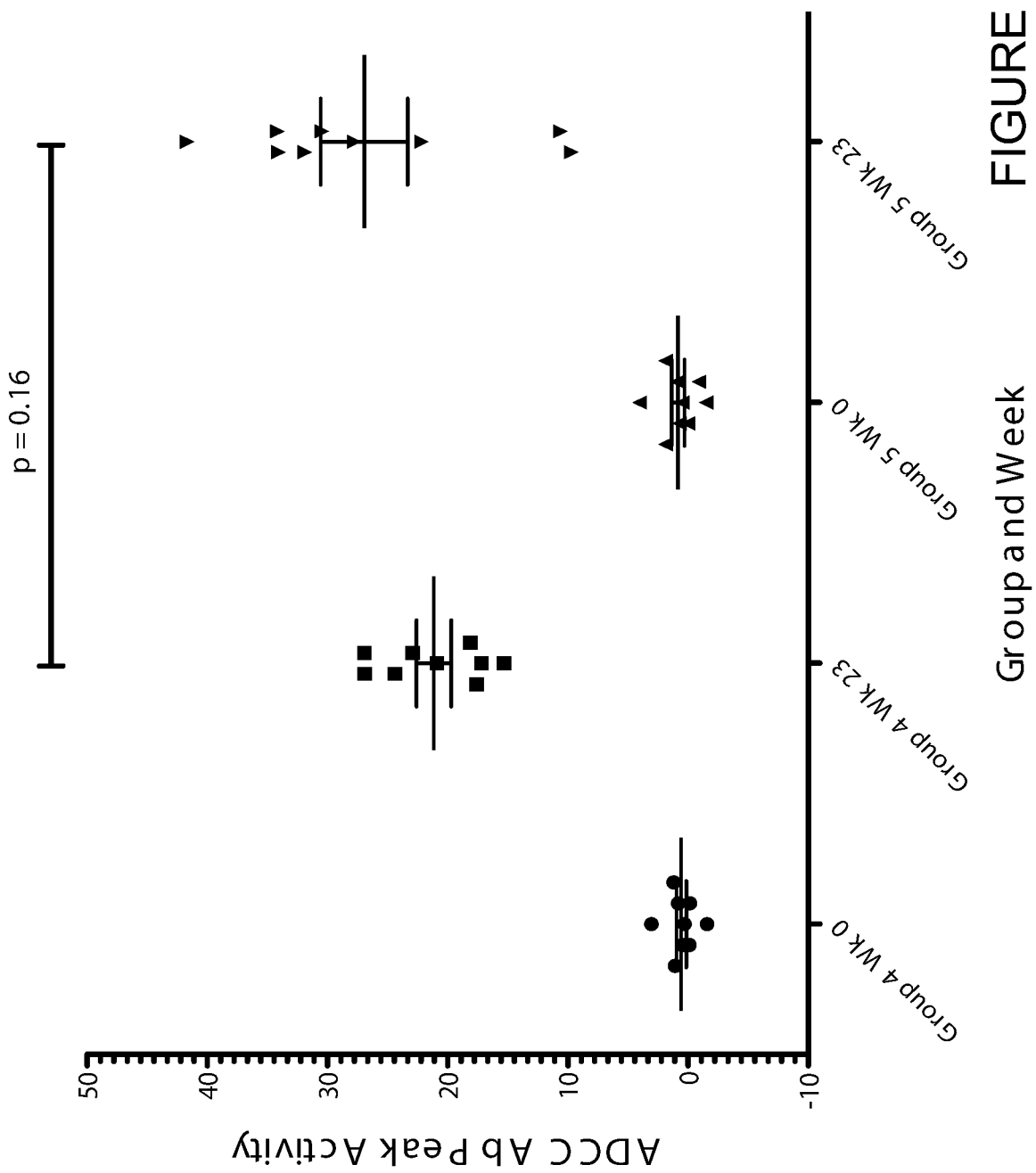
FIG. 15 shows ADCC with AE.A244 gp120-coated CD4 T cell targets NHP #64—Week 23—group 4 (B/E) vs. group 5 (B/E/E/E)

FIGS. 12-14 show data from NHP #64 Group 4 (B/E) and Group 5 (B/E/E/E/) animals in TZMbl and A3R5 Assays Neutralization Assays FIG. 15 show data from NHP #64 Group 4 (B/E) and Group 5 (B/E/E/E/) animals in ADCC with gp120-coated CD4 T cell targets, which measures killing of A244 go120-cated CD4 T cell targets. The data show a trend for group 5 (B/E/E/E+ALVAC boost) to give greater ADCC than group 4 (B/E+ALVAC boost) (Not statistically significant).

Figure 16:
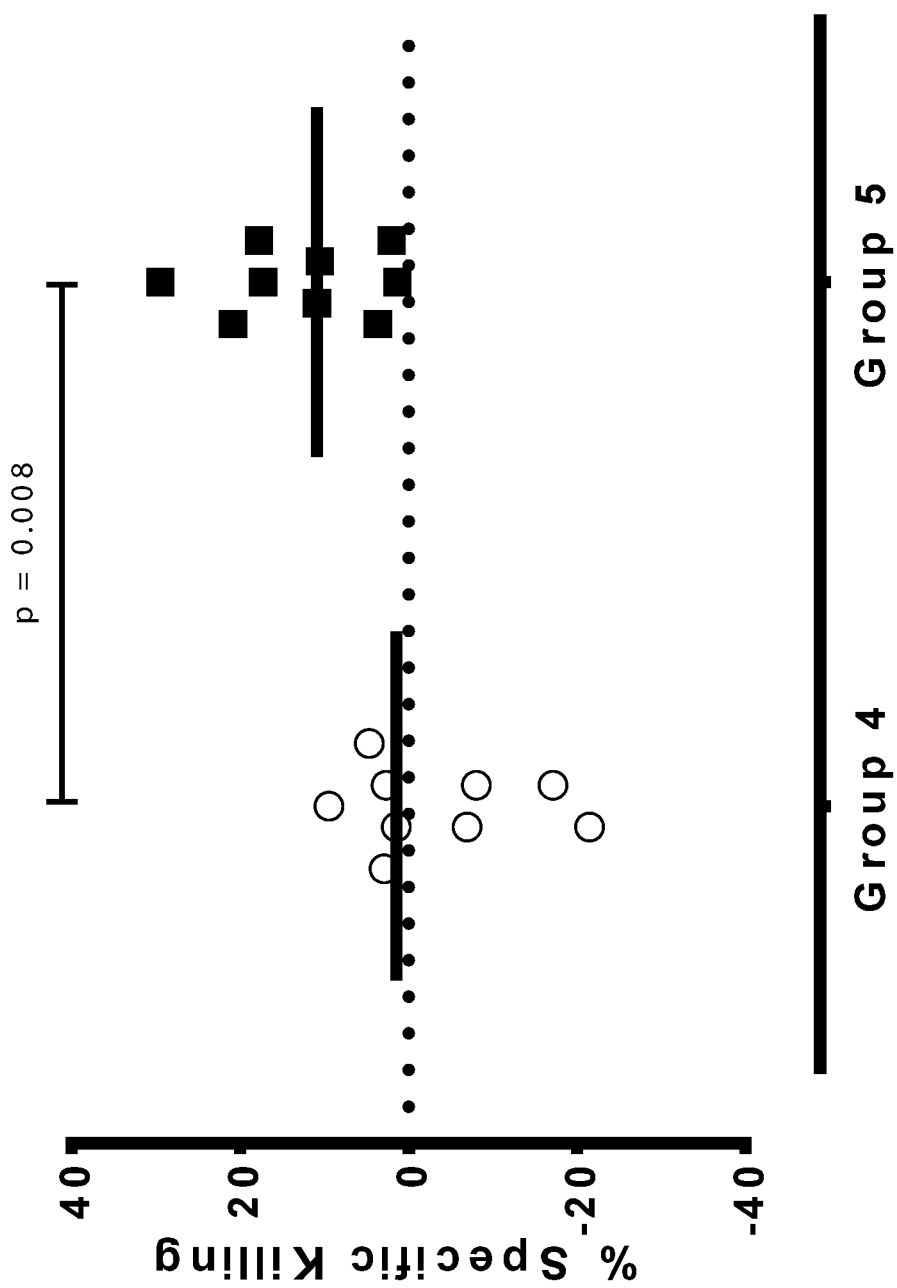
FIG. 16 shows ADCC with tier 2 CM235 virus-infected CD4 T cell targets—NHP 64 Group 4 vs 5 at dilution=1:100 Week 23 with Week 0 subtracted. Statistical comparisons are two-tailed Exact Wilcoxon tests.

FIG. 16 show data from NHP #64 Group 4 (B/E) and Group 5 (B/E/E/E/) animals in ADCC with AE.CM235 tier 2 primary virus infected CD4 T cell targets, which measures killing of AE.CM235-infected CD4 T cell targets. The data show significantly greater ADCC mediated by plasma from group 5 (B/E/E/E+ALVAC boost) than plasma from group 4 (B/E+ALVAC boost) (p=0.008).

In summary, there is: a trend in better binding to gp120s with plasma from pentavalent Envs regimen; no difference yet in neutralizations between the B/E and B/E/E/E/E groups; a trend for improved ADCC with gp120 coated CD4 T cell targets; significantly better ADCC with most biologically relevant ADCC assay: that using primary virus infected AE.CM235-infected CD4 T cells as targets.

Further plans for this NHP study include a boost the animals again before virus challenge (~May-June 2014) and then challenge with a relevant SHIV. There is a mutated SHIV 1157 tier 2 challenge virus to allow for CH58 and CH59 (the RV144 V2 putative protective Abs that target K169 in V2) to bind. Another virus, AE16 SHIV, is being titered IR, and would be available for challenge. Further experiments include: Challenge animals in NHP #64 study with AE/AE-like SHIV; Finish challenges with CH90 (ADCC, C1 that synergizes with CH58, V2, ADCC); Finish evaluation if CH58 UCA compared with V1V2 bnAb CH01 UCA mice; Finish evaluation of RV305. (See FIG. 17).

The contents of various publications and information referenced throughout the application are hereby incorporated by reference in their entirety.

SEQUENCE LISTING

```
<160> NUMBER OF SEQ ID NOS: 139

<210> SEQ ID NO 1
<211> LENGTH: 846
<212> TYPE: PRT
<213> ORGANISM: Human immunodeficiency virus

<400> SEQUENCE: 1

Met Arg Val Lys Glu Thr Gln Met Ile Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala His Gly Thr Glu Val
    50                  55                  60

His Asn Ile Trp Ala Thr His Ala Cys Val Pro Thr Asp Pro Asn Pro
65                  70                  75                  80

Gln Glu Ile His Leu Ala Asn Val Thr Glu Asn Phe Asn Met Trp Lys
                85                  90                  95

Asn Asn Met Val Glu Gln Met Gln Glu Asp Ile Ile Ser Leu Trp Asp
            100                 105                 110

Gln Ser Leu Lys Pro Cys Val Gln Leu Thr Pro Leu Cys Val Thr Leu
        115                 120                 125

Asn Cys Ala Ile Ala Asn Leu Thr Asn Ala Asn Ala Asn Leu Thr Asn
    130                 135                 140

Ile Asn Leu Asn Ile Thr Gly Asn Ile Thr Asp Glu Val Arg Asn Cys
145                 150                 155                 160

Thr Phe Asn Met Thr Thr Glu Ile Arg Asp Lys Lys Gln Lys Ala Tyr
                165                 170                 175

Ala Leu Phe Tyr Lys Leu Asp Leu Val Gln Leu Lys Asp Ser Asn Asp
            180                 185                 190

Ser Asn Arg Tyr Met Leu Ile Asn Cys Asn Thr Ser Val Ile Lys Gln
        195                 200                 205

Ala Cys Pro Lys Ile Ser Phe Asp Pro Ile Pro Ile His Tyr Cys Ala
    210                 215                 220

Pro Ala Gly Tyr Ala Ile Leu Lys Cys Asn Asp Lys Asn Phe Asn Gly
225                 230                 235                 240

Thr Gly Pro Cys Arg Asn Val Ser Ser Val Gln Cys Thr His Gly Ile
                245                 250                 255

Lys Pro Val Val Ser Thr Gln Leu Leu Leu Asn Gly Ser Leu Ala Glu
            260                 265                 270

Glu Glu Ile Ile Ile Arg Ser Glu Asn Leu Thr Asn Asn Ala Lys Thr
        275                 280                 285

Ile Ile Val His Leu Asn Lys Ser Val Glu Ile Asn Cys Thr Arg Pro
    290                 295                 300

Ser Asn Asn Thr Arg Thr Ser Ile Ser Ile Gly Pro Gly Gln Val Phe
```

```
           305                 310                 315                 320
Tyr Lys Thr Gly Asp Ile Ile Gly Asp Ile Lys Lys Ala Tyr Cys Glu
                325                 330                 335

Ile Asn Ala Thr Lys Trp Asn Glu Thr Leu Lys Gln Val Ile Gly Lys
                340                 345                 350

Leu Lys Glu His Phe Asn Asn Lys Thr Ile Ile Phe Gln Pro Pro Ser
                355                 360                 365

Gly Gly Asp Leu Glu Ile Thr Thr His His Phe Asn Cys Arg Gly Glu
370                 375                 380

Phe Phe Tyr Cys Asn Thr Ser Arg Leu Phe Lys Asn Glu Thr Glu Glu
385                 390                 395                 400

Val Asn Gly Thr Ile Ile Leu Pro Cys Arg Ile Lys Gln Ile Ile Asn
                405                 410                 415

Met Trp Gln Gly Val Gly Gln Ala Met Tyr Ala Pro Pro Ile Arg Gly
                420                 425                 430

Arg Ile Asn Cys Ile Ser Asn Ile Thr Gly Ile Leu Leu Thr Arg Asp
                435                 440                 445

Gly Gly Lys Asn Ala Ser Asn Glu Thr Phe Arg Pro Gly Gly Gly Asn
                450                 455                 460

Ile Lys Asp Asn Trp Arg Ser Glu Leu Tyr Lys Tyr Lys Val Val Gln
465                 470                 475                 480

Ile Glu Pro Leu Gly Ile Ala Pro Ser Arg Ala Arg Arg Val Val
                485                 490                 495

Glu Arg Glu Lys Arg Ala Val Gly Ile Gly Ala Met Ile Phe Gly Phe
                500                 505                 510

Leu Gly Ala Ala Gly Ser Thr Met Gly Ala Ala Ser Ile Thr Leu Thr
                515                 520                 525

Val Gln Ala Arg Gln Leu Leu Ser Gly Ile Val Gln Gln Ser Asn
                530                 535                 540

Leu Leu Arg Ala Ile Glu Ala Gln Gln His Leu Leu Gln Leu Thr Val
545                 550                 555                 560

Trp Gly Ile Lys Gln Leu Gln Ala Arg Val Leu Ala Val Glu Arg Tyr
                565                 570                 575

Leu Lys Asp Gln Gln Leu Leu Gly Leu Trp Gly Cys Ser Gly Lys Thr
                580                 585                 590

Ile Cys Thr Thr Ala Val Pro Trp Asn Ser Thr Trp Ser Asn Lys Ser
                595                 600                 605

Tyr Asp Glu Ile Trp Gly Asn Met Thr Trp Val Gln Trp Glu Arg Glu
610                 615                 620

Ile Ser Asn Tyr Thr Asn Gln Ile Tyr Glu Val Leu Met Glu Ser Gln
625                 630                 635                 640

Asn Gln Gln Asp Arg Asn Glu Lys Asp Leu Leu Glu Leu Asp Lys Trp
                645                 650                 655

Ala Ser Leu Trp Asn Trp Phe Asp Ile Thr Arg Trp Leu Trp Tyr Ile
                660                 665                 670

Lys Ile Phe Ile Met Ile Val Gly Gly Leu Ile Gly Leu Arg Ile Ile
                675                 680                 685

Phe Ala Val Leu Ser Ile Val Asn Arg Val Arg Gln Gly Tyr Ser Pro
                690                 695                 700

Leu Ser Leu Gln Ile Pro Thr His Gln Gln Arg Glu Pro Asp Arg Leu
705                 710                 715                 720

Glu Arg Ile Glu Glu Gly Gly Gly Glu Gln Asp Arg Asp Arg Ser Val
                725                 730                 735
```

```
Arg Leu Val Ser Gly Phe Phe Ala Leu Ala Trp Asp Leu Arg Ser
            740                 745                 750

Leu Cys Leu Phe Ser Tyr His Leu Leu Arg Asp Phe Ile Leu Ile Val
            755                 760                 765

Thr Arg Thr Val Val Lys Gly Leu Arg Arg Gly Trp Glu Gly Leu Lys
            770                 775                 780

Tyr Leu Gly Asn Leu Leu Leu Tyr Trp Gly Gln Glu Leu Lys Ile Ser
785                 790                 795                 800

Ala Ile Ser Leu Leu Asn Ala Thr Ala Ile Arg Val Gly Gly Trp Thr
                805                 810                 815

Asp Arg Val Ile Glu Val Ala Gln Gly Ala Trp Arg Ala Val Leu His
            820                 825                 830

Ile Pro Arg Arg Ile Arg Gln Gly Phe Glu Arg Ala Leu Leu
            835                 840                 845

<210> SEQ ID NO 2
<211> LENGTH: 861
<212> TYPE: PRT
<213> ORGANISM: Human immunodeficiency virus

<400> SEQUENCE: 2

Met Arg Val Lys Glu Thr Gln Met Asn Trp Pro Asn Trp Trp Lys Gly
1               5                   10                  15

Val Thr Leu Ile Leu Gly Leu Val Ile Ile Cys Arg Ala Ser Asp Asn
            20                  25                  30

Leu Trp Val Thr Val Tyr Tyr Gly Val Pro Val Trp Arg Asp Ala Glu
            35                  40                  45

Thr Thr Leu Phe Cys Ala Ser Asp Ala Lys Ala His Asp Thr Glu Val
            50                  55                  60

His Asn Val Trp Ala Thr His Ala Cys Val Pro Thr Asp Pro Asn Pro
65              70                  75                  80

Gln Glu Leu Tyr Leu Glu Asn Val Thr Glu Asn Phe Asn Met Trp Thr
                85                  90                  95

Asn Lys Met Val Glu Gln Met His Glu Asp Val Ile Ser Leu Trp Asp
            100                 105                 110

Gln Ser Leu Lys Pro Cys Ile Lys Leu Thr Pro Leu Cys Val Thr Leu
            115                 120                 125

Asn Cys Thr Asn Ala Met Phe Asn Asn Thr Asn Ala Asn Ser Thr Ala
            130                 135                 140

Ser Val Thr Thr Asp Asp Gly Thr Asn Arg Ile Gly Asn Leu Thr Asp
145                 150                 155                 160

Glu Val Lys Asn Cys Thr Phe Asn Val Thr Thr Glu Leu Lys Asp Lys
                165                 170                 175

Lys Gln Lys Val Tyr Ala Leu Phe Tyr Lys Leu Asp Ile Val Gln Met
            180                 185                 190

Pro Asn Ser Glu Tyr Arg Leu Ile Asn Cys Asn Thr Ser Val Ile Lys
            195                 200                 205

Gln Ala Cys Pro Lys Ile Thr Phe Asp Pro Ile Pro Ile His Tyr Cys
            210                 215                 220

Thr Pro Ala Gly Tyr Ala Ile Leu Lys Cys Asn Asp Lys Asn Phe Asn
225                 230                 235                 240

Gly Thr Gly Pro Cys Lys Asn Val Ser Ser Val Gln Cys Thr His Gly
                245                 250                 255

Ile Lys Pro Val Val Ser Thr Gln Leu Leu Leu Asn Gly Ser Leu Ala
```

```
                260                 265                 270
Glu Glu Glu Ile Ile Ile Arg Ser Glu Asn Leu Thr Asn Asn Ala Lys
            275                 280                 285

Thr Ile Ile Val His Phe Asn Lys Ser Val Glu Ile Asn Cys Thr Arg
        290                 295                 300

Pro Ser Asn Asn Thr Arg Thr Ser Val His Ile Gly Pro Gly Gln Val
305                 310                 315                 320

Phe Tyr Arg Thr Gly Asp Ile Ile Gly Asp Ile Arg Lys Ala Tyr Cys
                325                 330                 335

Glu Val Asn Gly Thr Arg Trp Asn Lys Val Leu Lys Gln Val Thr Asn
            340                 345                 350

Lys Leu Lys Glu Lys Phe His His Lys Thr Ile Lys Phe Gln Pro Pro
        355                 360                 365

Ser Gly Gly Asp Leu Glu Ile Thr Met Leu His Phe Asn Cys Arg Gly
    370                 375                 380

Glu Phe Phe Tyr Cys Asn Thr Thr Ser Leu Phe Asn Asp Thr Cys Ile
385                 390                 395                 400

Gly Asn Glu Thr Lys Glu Gly Cys Asn Thr Thr Ile Ile Leu Pro Cys
                405                 410                 415

Arg Ile Lys Gln Ile Val Asn Met Trp Gln Gly Val Gly Gln Ala Met
            420                 425                 430

Tyr Ala Pro Pro Ile Ser Gly Arg Ile Asn Cys Val Ser Asn Ile Thr
        435                 440                 445

Gly Ile Leu Leu Thr Arg Asp Gly Gly Val Asn Asn Asp Ser Ser Glu
    450                 455                 460

Ile Phe Arg Pro Gly Gly Gly Asp Ile Arg Asp Lys Trp Arg Ser Glu
465                 470                 475                 480

Leu Tyr Lys Tyr Lys Val Val Gln Ile Glu Pro Leu Gly Val Ala Pro
                485                 490                 495

Thr Arg Ala Lys Arg Arg Val Val Glu Arg Pro Lys Arg Ala Val Gly
            500                 505                 510

Ile Gly Ala Met Ile Phe Gly Phe Leu Gly Ala Ala Gly Ser Thr Met
        515                 520                 525

Gly Ala Ala Ser Ile Thr Leu Thr Val Gln Ala Arg Gln Leu Leu Ser
    530                 535                 540

Gly Ile Val Gln Gln Gln Ser Asn Leu Leu Arg Ala Ile Glu Ala Gln
545                 550                 555                 560

His His Leu Leu Gln Leu Thr Val Trp Gly Ile Lys Gln Leu Gln Ala
                565                 570                 575

Arg Val Leu Ala Val Glu Arg Tyr Leu Lys Asp Gln Lys Phe Leu Gly
            580                 585                 590

Leu Trp Gly Cys Ser Gly Lys Val Ile Cys Thr Thr Ala Val Pro Trp
        595                 600                 605

Asn Ser Thr Trp Ser Asn Lys Ser Tyr Asp Glu Ile Trp Asn Asn Met
    610                 615                 620

Thr Trp Ile Glu Trp Glu Arg Glu Ile Gly Asn Tyr Thr Ser Gln Ile
625                 630                 635                 640

Tyr Glu Ile Leu Thr Glu Ser Gln Asn Gln Asp Arg Asn Glu Lys
                645                 650                 655

Asp Leu Leu Ala Leu Asp His Trp Ala Ser Leu Trp Asn Trp Phe Asp
            660                 665                 670

Ile Thr Lys Trp Leu Trp Tyr Ile Lys Ile Phe Ile Met Ile Val Gly
        675                 680                 685
```

```
Gly Leu Ile Gly Leu Arg Ile Val Phe Ala Val Leu Ser Ile Val Asn
        690                 695                 700

Arg Val Arg Gln Gly Tyr Ser Pro Val Ser Phe Gln Ile Pro Thr His
705                 710                 715                 720

Gln Gln Arg Glu Pro Asp Arg Pro Glu Arg Ile Glu Glu Gly Gly Gly
                725                 730                 735

Glu Gln Asp Arg Asp Arg Ser Val Arg Leu Val Thr Gly Phe Leu Ala
                740                 745                 750

Leu Leu Trp Asp Asp Leu Arg Ser Leu Cys Leu Phe Ser Tyr His Arg
                755                 760                 765

Leu Arg Asp Leu Leu Ile Ala Lys Arg Thr Val Glu Leu Leu Gly
        770                 775                 780

Tyr Ser Ser Leu Lys Gly Leu Arg Arg Gly Trp Glu Ile Leu Lys Tyr
785                 790                 795                 800

Leu Gly Asn Leu Leu Tyr Trp Gly Arg Glu Leu Lys Ile Ser Ala
                805                 810                 815

Val Ser Leu Phe Asp Ala Ile Ala Ile Ala Val Ala Gly Trp Thr Asp
                820                 825                 830

Arg Val Ile Glu Val Val Gln Arg Ala Trp Arg Ala Ile Leu His Ile
        835                 840                 845

Pro Arg Arg Ile Arg Gln Gly Leu Glu Arg Ala Leu Leu
    850                 855                 860

<210> SEQ ID NO 3
<211> LENGTH: 856
<212> TYPE: PRT
<213> ORGANISM: Human immunodeficiency virus

<400> SEQUENCE: 3

Met Arg Val Lys Gly Thr Gln Met Asn Trp Pro Asn Leu Trp Arg Trp
1               5                   10                  15

Gly Thr Leu Ile Leu Gly Leu Val Ile Ile Cys Ser Ala Ser Asn Asn
                20                  25                  30

Leu Trp Val Thr Val Tyr Tyr Gly Val Pro Val Trp Lys Asp Ala Asp
            35                  40                  45

Thr Thr Leu Phe Cys Ala Ser Asp Ala Lys Ala His Glu Thr Glu Val
        50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Lys
                85                  90                  95

Asn Asn Met Val Glu Gln Met Gln Glu Asp Val Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Glu Ala Lys Leu Ser Gln Thr Ala Asn Asn Gln Thr Gly
        130                 135                 140

Asn Ile Thr Asp Gly Gly Asp Ile Gly Lys Ile Thr Glu Glu Val Lys
145                 150                 155                 160

Asn Cys Thr Phe Asn Met Thr Thr Glu Leu Arg Asp Lys Gln Gln Lys
                165                 170                 175

Val His Ala Leu Phe Tyr Arg Leu Asp Ile Val Gln Ile Asn Ser Asn
                180                 185                 190

Asp Asn Asn Ser Arg Glu Tyr Arg Leu Ile Asn Cys Asn Thr Ser Val
```

```
            195                 200                 205
Ile Lys Gln Ala Cys Pro Lys Val Ser Phe Asp Pro Ile Pro Ile His
210                 215                 220

Tyr Cys Thr Pro Ala Gly Tyr Ala Ile Leu Lys Cys Asn Asp Lys Lys
225                 230                 235                 240

Phe Asn Gly Thr Gly Pro Cys Lys Asn Val Ser Ser Val Gln Cys Thr
                    245                 250                 255

His Gly Ile Lys Pro Val Val Ser Thr Gln Leu Leu Leu Asn Gly Ser
                260                 265                 270

Leu Ala Glu Glu Asp Ile Ile Ile Arg Ser Glu Asn Leu Thr Asn Asn
            275                 280                 285

Ala Lys Asn Ile Ile Val Gln Phe Asn Lys Ser Val Glu Ile Asn Cys
        290                 295                 300

Thr Arg Pro Ser Asn Asn Thr Arg Thr Ser Val Ser Ile Gly Pro Gly
305                 310                 315                 320

Gln Val Phe Tyr Lys Thr Gly Asp Ile Ile Gly Asp Ile Arg Lys Ala
                325                 330                 335

Tyr Cys Glu Ile Asn Gly Thr Lys Trp Asn Glu Thr Leu Lys Gln Val
                340                 345                 350

Val Gly Lys Leu Arg Glu Tyr Phe Asn Lys Thr Ile Ile Phe Arg Pro
            355                 360                 365

Pro Ser Gly Gly Asp Leu Glu Ile Thr Thr His Tyr Phe Asn Cys Arg
370                 375                 380

Gly Glu Phe Phe Tyr Cys Asn Thr Thr Lys Leu Phe Asn Ser Thr Trp
385                 390                 395                 400

Thr Glu Asn Gly Thr Glu Glu Arg Phe Asn Asp Thr Ile Ile Leu Pro
                405                 410                 415

Cys Lys Ile Lys Gln Ile Val Asn Met Trp Gln Arg Ala Gly Gln Ala
                420                 425                 430

Met Tyr Asn Pro Pro Ile Lys Gly Lys Ile Asn Cys Val Ser Asn Ile
            435                 440                 445

Thr Gly Ile Ile Leu Ile Arg Asp Gly Gly Ala Asn Asn Thr Asn Asn
450                 455                 460

Asn Glu Thr Phe Arg Pro Gly Gly Gly Asn Ile Lys Asp Asn Trp Arg
465                 470                 475                 480

Ser Glu Leu Tyr Lys Tyr Lys Val Val Gln Ile Glu Pro Leu Gly Ile
                485                 490                 495

Ala Pro Thr Arg Ala Lys Arg Arg Val Val Glu Arg Glu Lys Arg Ala
                500                 505                 510

Val Gly Ile Gly Ala Met Ile Phe Gly Phe Leu Gly Ala Ala Gly Ser
            515                 520                 525

Thr Met Gly Ala Ala Ser Ile Thr Leu Thr Val Gln Ala Arg Gln Leu
530                 535                 540

Leu Ser Gly Ile Val Gln Gln Ser Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Val Leu Ala Val Glu Arg Tyr Leu Lys Asp Gln Lys Phe
            580                 585                 590

Leu Ala Leu Trp Gly Cys Ser Gly Lys Ile Ile Cys Thr Thr Thr Val
                595                 600                 605

Pro Trp Asn Ser Thr Trp Ser Asn Lys Ser Tyr Glu Asp Ile Trp Asn
610                 615                 620
```

```
Asn Met Thr Trp Thr Gln Trp Glu Arg Glu Ile Ser Asn Tyr Thr Asn
625                 630                 635                 640

Gln Ile Tyr Glu Ile Leu Thr Glu Ser Gln Thr Gln Gln Asp Lys Asn
                645                 650                 655

Glu Lys Asp Leu Leu Ala Met Asp Lys Trp Ala Thr Leu Trp Asn Trp
            660                 665                 670

Phe Asp Ile Thr Lys Trp Leu Trp Tyr Ile Arg Ile Phe Ile Ile Ile
                675                 680                 685

Val Gly Gly Leu Ile Gly Leu Arg Ile Ile Phe Ala Val Leu Ser Ile
690                 695                 700

Val Asn Arg Val Arg Gln Gly Tyr Ser Pro Leu Ser Phe Gln Ile Pro
705                 710                 715                 720

Ser His His Gln Arg Glu Pro Asp Arg Pro Glu Gly Thr Glu Glu Gly
                725                 730                 735

Gly Gly Glu Gln Gly Arg Asp Lys Ser Ile Arg Leu Val Ser Gly Phe
            740                 745                 750

Leu Ala Val Phe Trp Asp Asp Leu Arg Ser Leu Cys Leu Phe Ser Tyr
                755                 760                 765

His Leu Leu Arg Asp Phe Ser Leu Ile Ala Ala Arg Thr Val Glu Leu
770                 775                 780

Leu Leu Arg Arg Gly Trp Glu Gly Leu Lys Tyr Leu Gly Asn Leu Leu
785                 790                 795                 800

Ile Tyr Trp Gly Gln Glu Leu Lys Ile Ser Ala Ile Ser Leu Leu Asp
                805                 810                 815

Thr Ile Ala Ile Ala Val Ala Gly Trp Thr Asp Arg Ile Ile Glu Ala
            820                 825                 830

Ala Gln Arg Ala Gly Arg Ala Ile Leu His Ile Pro Arg Arg Ile Arg
                835                 840                 845

Gln Gly Leu Glu Arg Leu Leu Leu
    850                 855

<210> SEQ ID NO 4
<211> LENGTH: 31
<212> TYPE: PRT
<213> ORGANISM: Human immunodeficiency virus

<400> SEQUENCE: 4

Val Arg Asn Cys Ser Phe Asn Met Thr Thr Glu Leu Arg Asp Lys Lys
1               5                   10                  15

Gln Lys Val His Ala Leu Phe Tyr Lys Leu Asp Ile Val Pro Ile
            20                  25                  30

<210> SEQ ID NO 5
<211> LENGTH: 31
<212> TYPE: PRT
<213> ORGANISM: Human immunodeficiency virus

<400> SEQUENCE: 5

Val Arg Asn Cys Thr Phe Asn Met Thr Thr Glu Ile Arg Asp Lys Lys
1               5                   10                  15

Gln Lys Ala Tyr Ala Leu Phe Tyr Lys Leu Asp Leu Val Gln Leu
            20                  25                  30

<210> SEQ ID NO 6
<211> LENGTH: 31
<212> TYPE: PRT
<213> ORGANISM: Human immunodeficiency virus
```

<400> SEQUENCE: 6

Val Lys Asn Cys Thr Phe Asn Val Thr Thr Glu Leu Lys Asp Lys
1               5                   10                  15

Gln Lys Val Tyr Ala Leu Phe Tyr Lys Leu Asp Ile Val Gln Met
            20                  25                  30

<210> SEQ ID NO 7
<211> LENGTH: 31
<212> TYPE: PRT
<213> ORGANISM: Human immunodeficiency virus

<400> SEQUENCE: 7

Val Lys Asn Cys Thr Phe Asn Met Thr Thr Glu Leu Arg Asp Lys Gln
1               5                   10                  15

Gln Lys Val His Ala Leu Phe Tyr Arg Leu Asp Ile Val Gln Ile
            20                  25                  30

<210> SEQ ID NO 8
<211> LENGTH: 31
<212> TYPE: PRT
<213> ORGANISM: Human immunodeficiency virus

<400> SEQUENCE: 8

Val Arg Asn Cys Thr Phe Asn Met Thr Thr Glu Ile Arg Asp Lys Lys
1               5                   10                  15

Gln Lys Val Gln Ala Leu Phe Tyr Arg Leu Asp Ile Val Pro Ile
            20                  25                  30

<210> SEQ ID NO 9
<211> LENGTH: 31
<212> TYPE: PRT
<213> ORGANISM: Human immunodeficiency virus

<400> SEQUENCE: 9

Val Lys Asn Cys Ser Phe Lys Ile Thr Thr Glu Leu Arg Asp Lys Gln
1               5                   10                  15

Gln Lys Val Tyr Ala Leu Phe Tyr Lys Leu Asp Ile Val Gln Met
            20                  25                  30

<210> SEQ ID NO 10
<211> LENGTH: 31
<212> TYPE: PRT
<213> ORGANISM: Human immunodeficiency virus

<400> SEQUENCE: 10

Val Lys Asn Cys Thr Phe Asn Met Thr Thr Glu Leu Lys Asp Lys Lys
1               5                   10                  15

Lys Lys Val His Ala Leu Phe Tyr Lys Leu Asp Ile Val Gln Ile
            20                  25                  30

<210> SEQ ID NO 11
<211> LENGTH: 31
<212> TYPE: PRT
<213> ORGANISM: Human immunodeficiency virus

<400> SEQUENCE: 11

Val Arg Asn Cys Thr Phe Asn Met Thr Thr Glu Ile Arg Asp Lys Lys
1               5                   10                  15

Gln Lys Ala Tyr Ala Leu Phe Tyr Lys Leu Asp Leu Val Pro Leu
            20                  25                  30

<210> SEQ ID NO 12
<211> LENGTH: 31
<212> TYPE: PRT
<213> ORGANISM: Human immunodeficiency virus

<400> SEQUENCE: 12

Val Lys Asn Cys Thr Phe Asn Val Thr Thr Glu Leu Lys Asp Lys Lys
1               5                   10                  15

Gln Lys Val Tyr Ala Leu Phe Tyr Lys Leu Asp Ile Val Pro Met
            20                  25                  30

<210> SEQ ID NO 13
<211> LENGTH: 31
<212> TYPE: PRT
<213> ORGANISM: Human immunodeficiency virus

<400> SEQUENCE: 13

Val Lys Asn Cys Thr Phe Asn Met Thr Thr Glu Leu Arg Asp Lys Gln
1               5                   10                  15

Gln Lys Val His Ala Leu Phe Tyr Arg Leu Asp Ile Val Pro Ile
            20                  25                  30

<210> SEQ ID NO 14
<211> LENGTH: 31
<212> TYPE: PRT
<213> ORGANISM: Human immunodeficiency virus

<400> SEQUENCE: 14

Val Lys Asn Cys Ser Phe Lys Ile Thr Thr Val Leu Arg Asp Lys Gln
1               5                   10                  15

Gln Lys Val Tyr Ala Leu Phe Tyr Lys Leu Asp Ile Val Gln Met
            20                  25                  30

<210> SEQ ID NO 15
<211> LENGTH: 31
<212> TYPE: PRT
<213> ORGANISM: Human immunodeficiency virus

<400> SEQUENCE: 15

Val Arg Asn Cys Ser Phe Asn Met Thr Thr Glu Leu Arg Asp Lys Lys
1               5                   10                  15

Gln Lys Val His Ala Leu Phe Tyr Lys Leu Asp Ile Val Pro Ile
            20                  25                  30

<210> SEQ ID NO 16
<211> LENGTH: 31
<212> TYPE: PRT
<213> ORGANISM: Human immunodeficiency virus

<400> SEQUENCE: 16

Val Arg Asn Cys Ser Phe Asn Met Thr Thr Glu Leu Arg Asp Lys Lys
1               5                   10                  15

Gln Lys Val His Ala Leu Phe Tyr Lys Leu Asp Ile Val Pro Ile
            20                  25                  30

<210> SEQ ID NO 17
<211> LENGTH: 31
<212> TYPE: PRT
<213> ORGANISM: Human immunodeficiency virus

<400> SEQUENCE: 17

Val Arg Asn Cys Ser Phe Asn Met Thr Thr Glu Leu Arg Asp Lys Lys

```
1               5                   10                  15
Gln Lys Val Tyr Ala Leu Phe Tyr Lys Leu Asp Ile Val Gln Ile
            20                  25                  30

<210> SEQ ID NO 18
<211> LENGTH: 31
<212> TYPE: PRT
<213> ORGANISM: Human immunodeficiency virus

<400> SEQUENCE: 18

Val Arg Asn Cys Ser Phe Asn Met Thr Thr Glu Leu Arg Asp Lys Lys
1               5                   10                  15

Gln Lys Val His Ala Leu Phe Tyr Lys Leu Asp Ile Val Gln Ile
            20                  25                  30

<210> SEQ ID NO 19
<211> LENGTH: 31
<212> TYPE: PRT
<213> ORGANISM: Human immunodeficiency virus

<400> SEQUENCE: 19

Val Arg Asn Cys Ser Phe Asn Met Thr Thr Glu Leu Arg Asp Lys Lys
1               5                   10                  15

Gln Lys Val His Ala Leu Phe Tyr Lys Leu Asp Ile Val Gln Ile
            20                  25                  30

<210> SEQ ID NO 20
<211> LENGTH: 31
<212> TYPE: PRT
<213> ORGANISM: Human immunodeficiency virus

<400> SEQUENCE: 20

Ile Lys Asn Cys Ser Phe Asn Ile Ser Thr Ser Ile Arg Gly Lys Val
1               5                   10                  15

Gln Lys Glu Tyr Ala Phe Phe Tyr Lys Leu Asp Ile Ile Pro Ile
            20                  25                  30

<210> SEQ ID NO 21
<211> LENGTH: 31
<212> TYPE: PRT
<213> ORGANISM: Human immunodeficiency virus

<400> SEQUENCE: 21

Met Lys Asn Cys Ser Phe Asn Ile Thr Thr Ser Ile Arg Asp Lys Met
1               5                   10                  15

Gln Lys Glu Tyr Ala Leu Leu Tyr Lys Leu Asp Ile Val Ala Ile
            20                  25                  30

<210> SEQ ID NO 22
<211> LENGTH: 31
<212> TYPE: PRT
<213> ORGANISM: Human immunodeficiency virus

<400> SEQUENCE: 22

Val Arg Asn Cys Ser Phe Asn Met Thr Thr Glu Leu Arg Asp Lys Lys
1               5                   10                  15

Gln Lys Val His Ala Leu Phe Tyr Lys Leu Asp Ile Val Pro Ile
            20                  25                  30

<210> SEQ ID NO 23
<211> LENGTH: 31
<212> TYPE: PRT
```

<213> ORGANISM: Human immunodeficiency virus

<400> SEQUENCE: 23

Val Arg Asn Cys Thr Phe Asn Met Thr Thr Glu Ile Arg Asp Lys Lys
1 5 10 15

Gln Lys Ala Tyr Ala Leu Phe Tyr Lys Leu Asp Leu Val Gln Leu
20 25 30

<210> SEQ ID NO 24
<211> LENGTH: 31
<212> TYPE: PRT
<213> ORGANISM: Human immunodeficiency virus

<400> SEQUENCE: 24

Val Lys Asn Cys Thr Phe Asn Val Thr Thr Glu Leu Lys Asp Lys Lys
1 5 10 15

Gln Lys Val Tyr Ala Leu Phe Tyr Lys Leu Asp Ile Val Gln Met
20 25 30

<210> SEQ ID NO 25
<211> LENGTH: 31
<212> TYPE: PRT
<213> ORGANISM: Human immunodeficiency virus

<400> SEQUENCE: 25

Val Lys Asn Cys Thr Phe Asn Met Thr Thr Glu Leu Arg Asp Lys Gln
1 5 10 15

Gln Lys Val His Ala Leu Phe Tyr Arg Leu Asp Ile Val Gln Ile
20 25 30

<210> SEQ ID NO 26
<211> LENGTH: 31
<212> TYPE: PRT
<213> ORGANISM: Human immunodeficiency virus

<400> SEQUENCE: 26

Val Arg Asn Cys Ser Phe Asn Met Thr Thr Glu Leu Arg Asp Lys Lys
1 5 10 15

Gln Lys Val His Ala Leu Phe Tyr Lys Leu Asp Ile Val Pro Ile
20 25 30

<210> SEQ ID NO 27
<211> LENGTH: 31
<212> TYPE: PRT
<213> ORGANISM: Human immunodeficiency virus

<400> SEQUENCE: 27

Val Arg Asn Cys Thr Phe Asn Met Thr Thr Glu Ile Arg Asp Lys Lys
1 5 10 15

Gln Lys Val Gln Ala Leu Phe Tyr Arg Leu Asp Ile Val Pro Ile
20 25 30

<210> SEQ ID NO 28
<211> LENGTH: 31
<212> TYPE: PRT
<213> ORGANISM: Human immunodeficiency virus

<400> SEQUENCE: 28

Val Lys Asn Cys Ser Phe Lys Ile Thr Thr Glu Leu Arg Asp Lys Gln
1 5 10 15

Gln Lys Val Tyr Ala Leu Phe Tyr Lys Leu Asp Ile Val Gln Met
20 25 30

<210> SEQ ID NO 29
<211> LENGTH: 31
<212> TYPE: PRT
<213> ORGANISM: Human immunodeficiency virus

<400> SEQUENCE: 29

Val Lys Asn Cys Thr Phe Asn Met Thr Thr Glu Leu Lys Asp Lys Lys
1               5                   10                  15

Lys Lys Val His Ala Leu Phe Tyr Lys Leu Asp Ile Val Gln Ile
            20                  25                  30

<210> SEQ ID NO 30
<211> LENGTH: 31
<212> TYPE: PRT
<213> ORGANISM: Human immunodeficiency virus

<400> SEQUENCE: 30

Ile Lys Asn Cys Ser Phe Asn Met Thr Thr Glu Ile Arg Asp Lys Gln
1               5                   10                  15

Gln Lys Val Tyr Ala Leu Phe Tyr Lys Val Asp Ile Val Ser Met
            20                  25                  30

<210> SEQ ID NO 31
<211> LENGTH: 31
<212> TYPE: PRT
<213> ORGANISM: Human immunodeficiency virus

<400> SEQUENCE: 31

Val Lys Asn Cys Ser Phe Lys Ile Thr Thr Glu Leu Arg Asp Lys Gln
1               5                   10                  15

Gln Lys Val Tyr Ala Leu Phe Tyr Lys Leu Asp Ile Val Gln Met
            20                  25                  30

<210> SEQ ID NO 32
<211> LENGTH: 31
<212> TYPE: PRT
<213> ORGANISM: Human immunodeficiency virus

<400> SEQUENCE: 32

Val Gln Asn Cys Thr Phe Asn Met Thr Thr Val Val Ser Asp Arg Lys
1               5                   10                  15

Gln Gln Val Ser Ala Leu Phe Tyr Arg Leu Asp Ile Thr Gln Ile
            20                  25                  30

<210> SEQ ID NO 33
<211> LENGTH: 31
<212> TYPE: PRT
<213> ORGANISM: Human immunodeficiency virus

<400> SEQUENCE: 33

Val Thr Asn Cys Ser Phe Asn Met Thr Thr Glu Leu Thr Asp Lys Arg
1               5                   10                  15

Arg Met Val His Ala Leu Phe Tyr Arg Leu Asp Ile Val Pro Ile
            20                  25                  30

<210> SEQ ID NO 34
<211> LENGTH: 31
<212> TYPE: PRT
<213> ORGANISM: Human immunodeficiency virus

<400> SEQUENCE: 34

Val Lys Asn Cys Thr Phe Asn Met Thr Thr Glu Leu Lys Asp Lys
1               5                   10                  15

Lys Lys Val His Ala Leu Phe Tyr Lys Leu Asp Ile Val Gln Ile
            20                  25                  30

<210> SEQ ID NO 35
<211> LENGTH: 31
<212> TYPE: PRT
<213> ORGANISM: Human immunodeficiency virus

<400> SEQUENCE: 35

Val Arg Asn Cys Thr Phe Asn Thr Thr Thr Glu Leu Arg Asp Lys Lys
1               5                   10                  15

Gln Gln Val Tyr Ala Leu Phe Tyr Lys Leu Asp Ile Val Gln Ile
            20                  25                  30

<210> SEQ ID NO 36
<211> LENGTH: 31
<212> TYPE: PRT
<213> ORGANISM: Human immunodeficiency virus

<400> SEQUENCE: 36

Val Arg Asn Cys Thr Phe Asn Met Thr Thr Glu Ile Arg Asp Lys Gln
1               5                   10                  15

His Lys Val His Ala Leu Phe Tyr Lys Leu Asp Ile Val Gln Met
            20                  25                  30

<210> SEQ ID NO 37
<211> LENGTH: 31
<212> TYPE: PRT
<213> ORGANISM: Human immunodeficiency virus

<400> SEQUENCE: 37

Ala Arg Asn Cys Ser Phe Asn Val Thr Thr Glu Leu Arg Asp Lys Val
1               5                   10                  15

Gln Glu Val Tyr Ala Leu Phe Tyr Lys Leu Asp Ile Val Gln Ile
            20                  25                  30

<210> SEQ ID NO 38
<211> LENGTH: 31
<212> TYPE: PRT
<213> ORGANISM: Human immunodeficiency virus

<400> SEQUENCE: 38

Ile Arg Asn Cys Thr Phe Asn Met Thr Thr Glu Leu Lys Asp Lys Lys
1               5                   10                  15

Gln Lys Val His Ala Leu Phe Tyr Lys Leu Asp Ile Val Gln Met
            20                  25                  30

<210> SEQ ID NO 39
<211> LENGTH: 31
<212> TYPE: PRT
<213> ORGANISM: Human immunodeficiency virus

<400> SEQUENCE: 39

Ala Lys Asn Cys Ser Phe Asn Met Ala Thr Glu Leu Arg Asp Lys Lys
1               5                   10                  15

Gln Lys Val Gln Ala Leu Phe Tyr Lys Leu Asp Ile Val Pro Ile
            20                  25                  30

<210> SEQ ID NO 40
<211> LENGTH: 31

```
<212> TYPE: PRT
<213> ORGANISM: Human immunodeficiency virus

<400> SEQUENCE: 40

Val Arg Asn Cys Ser Phe Asn Met Thr Thr Glu Leu Arg Asp Lys Lys
1               5                   10                  15

Gln Lys Phe Tyr Ala Leu Phe Tyr Lys Leu Asp Ile Val Ser Ile
            20                  25                  30

<210> SEQ ID NO 41
<211> LENGTH: 31
<212> TYPE: PRT
<213> ORGANISM: Human immunodeficiency virus

<400> SEQUENCE: 41

Met Lys Asn Cys Ser Phe Asn Met Thr Thr Glu Leu Lys Asp Lys Lys
1               5                   10                  15

Gln Lys Val His Ala Leu Phe Tyr Glu Leu Asp Ile Val Gln Ile
            20                  25                  30

<210> SEQ ID NO 42
<211> LENGTH: 31
<212> TYPE: PRT
<213> ORGANISM: Human immunodeficiency virus

<400> SEQUENCE: 42

Val Arg Asn Cys Ser Phe Asn Met Thr Thr Val Ile Arg Asp Lys Lys
1               5                   10                  15

Gln Gln Val His Ala Leu Phe Tyr Lys Leu Asp Ile Val Pro Ile
            20                  25                  30

<210> SEQ ID NO 43
<211> LENGTH: 31
<212> TYPE: PRT
<213> ORGANISM: Human immunodeficiency virus

<400> SEQUENCE: 43

Ile Ser Asn Cys Thr Phe Asn Met Thr Thr Glu Ile Arg Asp Lys Lys
1               5                   10                  15

Lys Lys Val His Ala Leu Phe Tyr Asn Leu Asp Ile Val Lys Ile
            20                  25                  30

<210> SEQ ID NO 44
<211> LENGTH: 31
<212> TYPE: PRT
<213> ORGANISM: Human immunodeficiency virus

<400> SEQUENCE: 44

Val Arg Asn Cys Thr Phe Asn Val Thr Thr Glu Leu Arg Asp Lys Lys
1               5                   10                  15

Gln Lys Val His Ala Leu Phe Tyr Arg Ile Asp Ile Val Pro Ile
            20                  25                  30

<210> SEQ ID NO 45
<211> LENGTH: 31
<212> TYPE: PRT
<213> ORGANISM: Human immunodeficiency virus

<400> SEQUENCE: 45

Val Lys Asn Cys Thr Phe Asn Met Thr Thr Glu Leu Arg Asp Lys Gln
1               5                   10                  15

Gln Lys Val His Ala Leu Phe Tyr Arg Leu Asp Ile Val Gln Ile
```

```
                  20                  25                  30

<210> SEQ ID NO 46
<211> LENGTH: 31
<212> TYPE: PRT
<213> ORGANISM: Human immunodeficiency virus

<400> SEQUENCE: 46

Val Arg Asn Cys Ser Phe Asn Met Thr Thr Glu Leu Arg Asp Lys Lys
1               5                   10                  15

Gln Lys Val His Ala Leu Phe Tyr Lys Leu Asp Ile Val Pro Met
            20                  25                  30

<210> SEQ ID NO 47
<211> LENGTH: 31
<212> TYPE: PRT
<213> ORGANISM: Human immunodeficiency virus

<400> SEQUENCE: 47

Ile Arg Asn Cys Ser Phe Asn Val Thr Thr Glu Leu Lys Asp Lys Lys
1               5                   10                  15

Gln Lys Thr Tyr Ala Leu Phe Tyr Lys Leu Asp Leu Val Gln Ile
            20                  25                  30

<210> SEQ ID NO 48
<211> LENGTH: 31
<212> TYPE: PRT
<213> ORGANISM: Human immunodeficiency virus

<400> SEQUENCE: 48

Val Lys Asn Cys Ser Phe Asn Met Thr Thr Glu Val Arg Asp Lys Lys
1               5                   10                  15

Gln Lys Val His Ala Leu Phe Tyr Lys Leu Asp Ile Val Gln Ile
            20                  25                  30

<210> SEQ ID NO 49
<211> LENGTH: 31
<212> TYPE: PRT
<213> ORGANISM: Human immunodeficiency virus

<400> SEQUENCE: 49

Val Lys Asn Cys Ser Phe Lys Met Thr Thr Val Leu Arg Asp Lys Arg
1               5                   10                  15

Gln Gln Val His Ala Leu Phe Tyr Lys Leu Asp Val Val Pro Ile
            20                  25                  30

<210> SEQ ID NO 50
<211> LENGTH: 31
<212> TYPE: PRT
<213> ORGANISM: Human immunodeficiency virus

<400> SEQUENCE: 50

Ile Arg Asn Cys Ser Phe Asn Met Thr Thr Glu Leu Lys Asp Arg Lys
1               5                   10                  15

Gln Lys Val Tyr Ala Leu Phe Tyr Lys Pro Asp Ile Val Pro Leu
            20                  25                  30

<210> SEQ ID NO 51
<211> LENGTH: 31
<212> TYPE: PRT
<213> ORGANISM: Human immunodeficiency virus

<400> SEQUENCE: 51
```

Val Arg Asn Cys Ser Phe Asn Met Thr Thr Ile Leu Lys Asp Lys
1               5                   10                  15

Gln Gln Val His Ala Leu Phe Tyr Lys Leu Asp Ile Val Pro Ile
            20                  25                  30

<210> SEQ ID NO 52
<211> LENGTH: 31
<212> TYPE: PRT
<213> ORGANISM: Human immunodeficiency virus

<400> SEQUENCE: 52

Val Lys Asn Cys Thr Phe Asn Met Thr Thr Glu Ile Arg Asp Lys Glu
1               5                   10                  15

Gln Gln Ile His Ala Leu Phe Tyr Lys Leu Asp Ile Val Gln Ile
            20                  25                  30

<210> SEQ ID NO 53
<211> LENGTH: 31
<212> TYPE: PRT
<213> ORGANISM: Human immunodeficiency virus

<400> SEQUENCE: 53

Val Arg Asn Cys Thr Phe Asn Met Thr Thr Glu Ile Arg Asp Lys Lys
1               5                   10                  15

Gln Lys Val Gln Ala Leu Phe Tyr Arg Leu Asp Ile Val Pro Ile
            20                  25                  30

<210> SEQ ID NO 54
<211> LENGTH: 31
<212> TYPE: PRT
<213> ORGANISM: Human immunodeficiency virus

<400> SEQUENCE: 54

Val Lys Asn Cys Thr Phe Asn Met Ser Thr Glu Leu Arg Asp Lys Lys
1               5                   10                  15

His Lys Val Tyr Ala Leu Phe Tyr Lys Leu Asp Ile Val Pro Leu
            20                  25                  30

<210> SEQ ID NO 55
<211> LENGTH: 31
<212> TYPE: PRT
<213> ORGANISM: Human immunodeficiency virus

<400> SEQUENCE: 55

Val Thr Asn Cys Thr Phe Asn Met Pro Thr Glu Ile Lys Asp Arg Lys
1               5                   10                  15

Gln Gln Ile Ser Ala Leu Phe Tyr Lys Leu Asp Ile Val Asn Ser
            20                  25                  30

<210> SEQ ID NO 56
<211> LENGTH: 31
<212> TYPE: PRT
<213> ORGANISM: Human immunodeficiency virus

<400> SEQUENCE: 56

Leu Lys Asn Cys Ser Phe Asn Thr Thr Thr Glu Leu Arg Asp Lys Lys
1               5                   10                  15

Gln Gln Val His Ala Leu Phe Tyr Lys Leu Asp Ile Val Gln Ile
            20                  25                  30

<210> SEQ ID NO 57

```
<211> LENGTH: 31
<212> TYPE: PRT
<213> ORGANISM: Human immunodeficiency virus

<400> SEQUENCE: 57

Ile Arg Asn Cys Thr Phe Asn Met Thr Thr Glu Ile Arg Asp Lys Gln
1               5                   10                  15

His Lys Val His Ala Leu Phe Tyr Lys Leu Asp Ile Val Glu Ile
            20                  25                  30

<210> SEQ ID NO 58
<211> LENGTH: 31
<212> TYPE: PRT
<213> ORGANISM: Human immunodeficiency virus

<400> SEQUENCE: 58

Val Lys Asn Cys Ser Phe Asn Ile Thr Thr Glu Ile Lys Asp Arg Lys
1               5                   10                  15

Lys Lys Val His Ala Leu Phe Tyr Arg Leu Asp Ile Val Gln Leu
            20                  25                  30

<210> SEQ ID NO 59
<211> LENGTH: 31
<212> TYPE: PRT
<213> ORGANISM: Human immunodeficiency virus

<400> SEQUENCE: 59

Ile Arg Asn Cys Thr Phe Asn Met Thr Thr Glu Val Thr Asp Lys Lys
1               5                   10                  15

Gln Lys Val His Ala Leu Phe Tyr Lys Leu Asp Ile Val Pro Met
            20                  25                  30

<210> SEQ ID NO 60
<211> LENGTH: 31
<212> TYPE: PRT
<213> ORGANISM: Human immunodeficiency virus

<400> SEQUENCE: 60

Val Lys Asn Cys Ser Phe Asn Met Thr Thr Glu Leu Arg Asp Lys Gln
1               5                   10                  15

Gln Asn Phe Tyr Ala Leu Phe Tyr Arg Leu Asp Ile Val Gln Ile
            20                  25                  30

<210> SEQ ID NO 61
<211> LENGTH: 31
<212> TYPE: PRT
<213> ORGANISM: Human immunodeficiency virus

<400> SEQUENCE: 61

Ile Arg Asn Cys Ser Phe Asn Ile Thr Thr Glu Ile Ile Asp Lys Lys
1               5                   10                  15

Lys Gln Val Tyr Ala Leu Phe Tyr Lys Leu Asp Thr Val Gln Ile
            20                  25                  30

<210> SEQ ID NO 62
<211> LENGTH: 31
<212> TYPE: PRT
<213> ORGANISM: Human immunodeficiency virus

<400> SEQUENCE: 62

Val Arg Asn Cys Ser Phe Asn Met Thr Thr Glu Leu Arg Asp Lys Lys
1               5                   10                  15
```

Gln Gln Ile Tyr Ala Leu Phe Tyr Lys Leu Asp Ile Val Pro Ile
            20                  25                  30

<210> SEQ ID NO 63
<211> LENGTH: 31
<212> TYPE: PRT
<213> ORGANISM: Human immunodeficiency virus

<400> SEQUENCE: 63

Val Arg Asn Cys Ser Phe Asn Ile Thr Thr Glu Leu Arg Asp Lys Gln
1               5                   10                  15

Arg Lys Val Gln Ala Leu Phe Tyr Arg Leu Asp Ile Ile Gln Thr
            20                  25                  30

<210> SEQ ID NO 64
<211> LENGTH: 31
<212> TYPE: PRT
<213> ORGANISM: Human immunodeficiency virus

<400> SEQUENCE: 64

Val Arg Asn Cys Ser Phe Asn Met Thr Thr Glu Leu Arg Asp Lys Lys
1               5                   10                  15

Gln Lys Val His Ala Leu Phe Tyr Lys Leu Asp Ile Val Pro Ile
            20                  25                  30

<210> SEQ ID NO 65
<211> LENGTH: 31
<212> TYPE: PRT
<213> ORGANISM: Human immunodeficiency virus

<400> SEQUENCE: 65

Val Lys Asn Cys Ser Phe Asn Thr Thr Thr Glu Leu Arg Asp Lys Lys
1               5                   10                  15

Gln Lys Ala Tyr Ala Leu Phe Tyr Lys Leu Asp Ile Val Gln Met
            20                  25                  30

<210> SEQ ID NO 66
<211> LENGTH: 31
<212> TYPE: PRT
<213> ORGANISM: Human immunodeficiency virus

<400> SEQUENCE: 66

Val Lys Asn Cys Ser Phe Asp Val Thr Thr Asp Leu Lys Asp Lys Thr
1               5                   10                  15

Gln Lys Asp His Ala Leu Phe Tyr Lys Leu Asp Ile Val Lys Ile
            20                  25                  30

<210> SEQ ID NO 67
<211> LENGTH: 31
<212> TYPE: PRT
<213> ORGANISM: Human immunodeficiency virus

<400> SEQUENCE: 67

Val Arg Asn Cys Ser Phe Asn Met Thr Thr Glu Leu Asn Asp Lys Lys
1               5                   10                  15

Gln Asn Ile His Ala Leu Phe Tyr Lys Leu Asp Ile Ile Gln Ile
            20                  25                  30

<210> SEQ ID NO 68
<211> LENGTH: 31
<212> TYPE: PRT
<213> ORGANISM: Human immunodeficiency virus

<400> SEQUENCE: 68

Val Arg Asn Cys Ser Phe Asn Ile Thr Thr Glu Leu Arg Asp Lys Gln
1               5                   10                  15

Arg Lys Val Gln Ala Leu Phe Tyr Arg Leu Asp Ile Ile Gln Thr
            20                  25                  30

<210> SEQ ID NO 69
<211> LENGTH: 31
<212> TYPE: PRT
<213> ORGANISM: Human immunodeficiency virus

<400> SEQUENCE: 69

Val Arg Asn Cys Thr Phe Asn Val Thr Thr Glu Ile Arg Asp Lys Lys
1               5                   10                  15

Lys Asn Val Tyr Ala Leu Phe Tyr Lys Leu Asp Leu Val Gln Met
            20                  25                  30

<210> SEQ ID NO 70
<211> LENGTH: 31
<212> TYPE: PRT
<213> ORGANISM: Human immunodeficiency virus

<400> SEQUENCE: 70

Val Arg Asn Cys Ser Phe Asn Met Thr Thr Glu Leu Arg Asp Lys Lys
1               5                   10                  15

Gln Lys Val Tyr Ala Leu Phe Tyr Lys Leu Asp Ile Val Pro Ile
            20                  25                  30

<210> SEQ ID NO 71
<211> LENGTH: 31
<212> TYPE: PRT
<213> ORGANISM: Human immunodeficiency virus

<400> SEQUENCE: 71

Val Arg Asn Cys Ser Phe Asn Ile Thr Thr Glu Ile Ile Asp Lys Lys
1               5                   10                  15

Gln Arg Val Gln Ala Leu Phe Tyr Lys Leu Asp Ile Val Pro Ile
            20                  25                  30

<210> SEQ ID NO 72
<211> LENGTH: 31
<212> TYPE: PRT
<213> ORGANISM: Human immunodeficiency virus

<400> SEQUENCE: 72

Met Lys Asn Cys Ser Phe Asn Met Thr Thr Glu Leu Arg Asp Lys Lys
1               5                   10                  15

Gln Lys Val His Ala Leu Phe Tyr Lys Leu Asp Ile Val Gln Met
            20                  25                  30

<210> SEQ ID NO 73
<211> LENGTH: 31
<212> TYPE: PRT
<213> ORGANISM: Human immunodeficiency virus

<400> SEQUENCE: 73

Val Lys Asn Cys Ser Phe Asn Met Thr Thr Glu Ile Arg Asp Arg Gln
1               5                   10                  15

Gln Lys Val His Ala Leu Phe Tyr Lys Leu Asp Ile Val Pro Leu
            20                  25                  30

<210> SEQ ID NO 74
<211> LENGTH: 31
<212> TYPE: PRT
<213> ORGANISM: Human immunodeficiency virus

<400> SEQUENCE: 74

Val Arg Asn Cys Thr Phe Asn Met Thr Thr Val Val Ser Asp Lys Lys
1               5                   10                  15

Gln Lys Val Tyr Ala Leu Phe Tyr Lys Leu Asp Leu Val Pro Met
            20                  25                  30

<210> SEQ ID NO 75
<211> LENGTH: 31
<212> TYPE: PRT
<213> ORGANISM: Human immunodeficiency virus

<400> SEQUENCE: 75

Ile Arg Asn Cys Ser Phe Asn Met Thr Thr Glu Leu Arg Asp Lys Arg
1               5                   10                  15

Gln Thr Val Tyr Ala Leu Phe Tyr Lys Leu Asp Val Val Pro Ile
            20                  25                  30

<210> SEQ ID NO 76
<211> LENGTH: 31
<212> TYPE: PRT
<213> ORGANISM: Human immunodeficiency virus

<400> SEQUENCE: 76

Val Lys Asn Cys Ser Phe Asn Met Thr Thr Glu Ile Ile Asp Lys Lys
1               5                   10                  15

Gln Lys Phe Tyr Ala Leu Phe Tyr Lys Leu Asp Ile Ile Gln Ile
            20                  25                  30

<210> SEQ ID NO 77
<211> LENGTH: 31
<212> TYPE: PRT
<213> ORGANISM: Human immunodeficiency virus

<400> SEQUENCE: 77

Val Lys Asn Cys Ser Phe Asn Met Thr Thr Glu Ile His Asp Arg Lys
1               5                   10                  15

Gln Lys Val His Ala Leu Phe Tyr Lys Leu Asp Ile Val Pro Ile
            20                  25                  30

<210> SEQ ID NO 78
<211> LENGTH: 31
<212> TYPE: PRT
<213> ORGANISM: Human immunodeficiency virus

<400> SEQUENCE: 78

Val Lys Asn Cys Ser Phe Asn Val Thr Thr Glu Leu Arg Asp Lys Gln
1               5                   10                  15

Lys Gln Ile His Ala Leu Phe Tyr Met Leu Asp Ile Val Ser Ile
            20                  25                  30

<210> SEQ ID NO 79
<211> LENGTH: 31
<212> TYPE: PRT
<213> ORGANISM: Human immunodeficiency virus

<400> SEQUENCE: 79

Val Lys Asn Cys Thr Phe Asn Met Thr Thr Glu Leu Thr Asp Lys Lys
1               5                   10                  15

```
Lys Lys Ala Tyr Ser Leu Phe Tyr Arg Leu Asp Ile Val Pro Ile
            20                  25                  30
```

<210> SEQ ID NO 80
<211> LENGTH: 31
<212> TYPE: PRT
<213> ORGANISM: Human immunodeficiency virus

<400> SEQUENCE: 80

```
Ile Lys Asn Cys Thr Phe Asn Met Thr Thr Asp Leu Lys Asp Lys Lys
1               5                   10                  15

Arg Lys Val His Ala Leu Phe Tyr Thr Leu Asp Ile Val Gln Ile
            20                  25                  30
```

<210> SEQ ID NO 81
<211> LENGTH: 31
<212> TYPE: PRT
<213> ORGANISM: Human immunodeficiency virus

<400> SEQUENCE: 81

```
Val Arg Asn Cys Ser Phe Asn Ile Thr Thr Glu Leu Arg Asp Lys Lys
1               5                   10                  15

Gln Arg Ala Tyr Ala Leu Phe Tyr Lys Leu Asp Ile Val Pro Ile
            20                  25                  30
```

<210> SEQ ID NO 82
<211> LENGTH: 31
<212> TYPE: PRT
<213> ORGANISM: Human immunodeficiency virus

<400> SEQUENCE: 82

```
Val Arg Asn Cys Ser Phe Asn Met Thr Thr Glu Leu Lys Asp Lys Lys
1               5                   10                  15

Gln Lys Val His Ala Leu Phe Tyr Met Leu Asp Ile Val Gln Ile
            20                  25                  30
```

<210> SEQ ID NO 83
<211> LENGTH: 31
<212> TYPE: PRT
<213> ORGANISM: Human immunodeficiency virus

<400> SEQUENCE: 83

```
Val Arg Asn Cys Ser Phe Asn Met Thr Thr Glu Ile Arg Asp Lys Lys
1               5                   10                  15

Gln Lys Val His Ala Leu Phe Tyr Arg Leu Asp Ile Val Pro Ile
            20                  25                  30
```

<210> SEQ ID NO 84
<211> LENGTH: 31
<212> TYPE: PRT
<213> ORGANISM: Human immunodeficiency virus

<400> SEQUENCE: 84

```
Ile Arg Asn Cys Thr Phe Asn Met Thr Thr Glu Ile Arg Asp Lys Lys
1               5                   10                  15

Gln Glu Thr Tyr Ala Leu Phe Tyr Lys Leu Asp Ile Val Pro Ile
            20                  25                  30
```

<210> SEQ ID NO 85
<211> LENGTH: 31
<212> TYPE: PRT
<213> ORGANISM: Human immunodeficiency virus

```
<400> SEQUENCE: 85

Val Lys Asn Cys Thr Phe Asn Met Thr Thr Glu Val Gln Asp Lys Lys
1               5                   10                  15

Gln Glu Val His Ala Leu Phe Tyr Glu Leu Asp Ile Val Gln Ile
            20                  25                  30

<210> SEQ ID NO 86
<211> LENGTH: 31
<212> TYPE: PRT
<213> ORGANISM: Human immunodeficiency virus

<400> SEQUENCE: 86

Val Lys Asn Cys Ser Phe Asn Ile Thr Thr Glu Leu Arg Asp Lys Lys
1               5                   10                  15

Gln Lys Ala Tyr Ala Leu Phe Tyr Ser Leu Asp Ile Val Pro Ile
            20                  25                  30

<210> SEQ ID NO 87
<211> LENGTH: 31
<212> TYPE: PRT
<213> ORGANISM: Human immunodeficiency virus

<400> SEQUENCE: 87

Val Arg Asn Cys Ser Phe Asn Met Thr Thr Val Leu Arg Asp Gln Arg
1               5                   10                  15

Gln Lys Val Tyr Ala Leu Phe Tyr Lys Leu Asp Ile Val Gln Ile
            20                  25                  30

<210> SEQ ID NO 88
<211> LENGTH: 31
<212> TYPE: PRT
<213> ORGANISM: Human immunodeficiency virus

<400> SEQUENCE: 88

Val Arg Asn Cys Ser Phe Asn Met Thr Thr Glu Ile Gln Asp Lys Lys
1               5                   10                  15

Gln Lys Val Tyr Ala Leu Phe Tyr Lys Leu Asp Ile Val Gln Ile
            20                  25                  30

<210> SEQ ID NO 89
<211> LENGTH: 31
<212> TYPE: PRT
<213> ORGANISM: Human immunodeficiency virus

<400> SEQUENCE: 89

Met Lys Asn Cys Ser Phe Asn Met Thr Thr Glu Leu Lys Asp Lys Lys
1               5                   10                  15

Gln Lys Val Tyr Ala Leu Phe Tyr Thr Leu Asp Ile Val Gln Met
            20                  25                  30

<210> SEQ ID NO 90
<211> LENGTH: 31
<212> TYPE: PRT
<213> ORGANISM: Human immunodeficiency virus

<400> SEQUENCE: 90

Val Arg Asn Cys Ser Phe Asn Met Thr Thr Glu Leu Glu Asp Lys Lys
1               5                   10                  15

Arg Arg Val His Ala Leu Phe Tyr Arg Leu Asp Leu Val Lys Ile
            20                  25                  30
```

<210> SEQ ID NO 91
<211> LENGTH: 31
<212> TYPE: PRT
<213> ORGANISM: Human immunodeficiency virus

<400> SEQUENCE: 91

Val Arg Asn Cys Ser Phe Asn Met Thr Thr Glu Leu Arg Asp Lys Lys
1               5                   10                  15

Gln Lys Val His Ala Leu Phe Tyr Arg Leu Asp Leu Val Gln Met
            20                  25                  30

<210> SEQ ID NO 92
<211> LENGTH: 31
<212> TYPE: PRT
<213> ORGANISM: Human immunodeficiency virus

<400> SEQUENCE: 92

Val Lys Asn Cys Ser Phe Lys Met Thr Thr Glu Leu Lys Asp Lys Lys
1               5                   10                  15

Lys Lys Val Tyr Ala Leu Phe Tyr Lys Leu Asp Ile Val Gln Met
            20                  25                  30

<210> SEQ ID NO 93
<211> LENGTH: 31
<212> TYPE: PRT
<213> ORGANISM: Human immunodeficiency virus

<400> SEQUENCE: 93

Val Lys Asn Cys Ser Phe Asn Met Thr Thr Leu Leu Thr Asp Lys Lys
1               5                   10                  15

Gln Lys Val His Ala Leu Phe Tyr Arg Leu Asp Ile Val Pro Ile
            20                  25                  30

<210> SEQ ID NO 94
<211> LENGTH: 31
<212> TYPE: PRT
<213> ORGANISM: Human immunodeficiency virus

<400> SEQUENCE: 94

Val Arg Asn Cys Ser Phe Asn Met Thr Thr Glu Leu Arg Asp Lys Lys
1               5                   10                  15

His Gln Val Tyr Ala Leu Phe Tyr Lys Leu Asp Ile Val Pro Ile
            20                  25                  30

<210> SEQ ID NO 95
<211> LENGTH: 31
<212> TYPE: PRT
<213> ORGANISM: Human immunodeficiency virus

<400> SEQUENCE: 95

Ile Ser Asn Cys Ser Phe Arg Met Thr Thr Glu Leu Arg Asp Lys Lys
1               5                   10                  15

Gln Lys Val His Ala Leu Phe Tyr Asn Leu Asp Ile Val Lys Ile
            20                  25                  30

<210> SEQ ID NO 96
<211> LENGTH: 31
<212> TYPE: PRT
<213> ORGANISM: Human immunodeficiency virus

<400> SEQUENCE: 96

Val Lys Asn Cys Thr Phe Asn Met Thr Thr Glu Leu Arg Asp Lys Lys

-continued

```
                1               5                  10                  15
Gln Lys Val His Ala Leu Phe Tyr Arg Leu Asp Ile Val Gln Leu
            20                  25                  30

<210> SEQ ID NO 97
<211> LENGTH: 31
<212> TYPE: PRT
<213> ORGANISM: Human immunodeficiency virus

<400> SEQUENCE: 97

Ser Met Asn Cys Thr Phe Asn Met Thr Thr Glu Ile Lys Asp Lys Lys
1               5                   10                  15
Thr Lys Val Asn Ala Leu Phe Tyr Lys Leu Asp Ile Val Gln Met
            20                  25                  30

<210> SEQ ID NO 98
<211> LENGTH: 31
<212> TYPE: PRT
<213> ORGANISM: Human immunodeficiency virus

<400> SEQUENCE: 98

Val Arg Asn Cys Ser Phe Asn Met Thr Thr Glu Leu Arg Asp Lys Lys
1               5                   10                  15
Gln Lys Val Tyr Ala Leu Phe Tyr Lys Leu Asp Ile Val Gln Ile
            20                  25                  30

<210> SEQ ID NO 99
<211> LENGTH: 31
<212> TYPE: PRT
<213> ORGANISM: Human immunodeficiency virus

<400> SEQUENCE: 99

Val Ser Asn Cys Thr Phe Ser Met Thr Thr Glu Leu Ala Asp Arg Lys
1               5                   10                  15
Gln Lys Val Tyr Ala Leu Phe Tyr Lys Leu Asp Ile Val Pro Val
            20                  25                  30

<210> SEQ ID NO 100
<211> LENGTH: 31
<212> TYPE: PRT
<213> ORGANISM: Human immunodeficiency virus

<400> SEQUENCE: 100

Val Arg Asn Cys Ser Phe Asn Ile Thr Thr Glu Ile Arg Asp Lys Lys
1               5                   10                  15
Lys Gln Val Gln Ala Leu Phe Tyr Lys Leu Asp Ile Val Gln Met
            20                  25                  30

<210> SEQ ID NO 101
<211> LENGTH: 31
<212> TYPE: PRT
<213> ORGANISM: Human immunodeficiency virus

<400> SEQUENCE: 101

Val Arg Asn Cys Ser Phe Asn Met Thr Thr Glu Ile Arg Asp Lys Lys
1               5                   10                  15
Gln Lys Val His Ala Leu Phe Tyr Lys Leu Asp Ile Val Gln Ile
            20                  25                  30

<210> SEQ ID NO 102
<211> LENGTH: 31
<212> TYPE: PRT
```

<213> ORGANISM: Human immunodeficiency virus

<400> SEQUENCE: 102

Val Lys Asn Cys Ser Phe Asn Met Thr Thr Glu Leu Thr Asp Lys Lys
1               5                   10                  15

Gln Lys Ala Tyr Ser Leu Phe Tyr Arg Leu Asp Ile Val Ser Ile
            20                  25                  30

<210> SEQ ID NO 103
<211> LENGTH: 31
<212> TYPE: PRT
<213> ORGANISM: Human immunodeficiency virus

<400> SEQUENCE: 103

Val Lys Asn Cys Thr Phe Asn Met Thr Thr Glu Leu Arg Asp Lys Lys
1               5                   10                  15

Gln Gln Val Arg Ala Leu Phe Tyr Lys Leu Asp Val Val Pro Met
            20                  25                  30

<210> SEQ ID NO 104
<211> LENGTH: 31
<212> TYPE: PRT
<213> ORGANISM: Human immunodeficiency virus

<400> SEQUENCE: 104

Val Arg Asn Cys Ser Phe Ser Met Thr Thr Glu Ile Arg Asp Lys Lys
1               5                   10                  15

Gln Lys Val Tyr Ala Leu Phe Tyr Lys Ile Asp Thr Val Ser Ile
            20                  25                  30

<210> SEQ ID NO 105
<211> LENGTH: 31
<212> TYPE: PRT
<213> ORGANISM: Human immunodeficiency virus

<400> SEQUENCE: 105

Val Arg Asn Cys Ser Phe Asn Met Thr Thr Glu Ile Arg Asp Lys Gln
1               5                   10                  15

Gln Lys Leu His Ala Leu Phe Tyr Lys Leu Asp Ile Val Gln Ile
            20                  25                  30

<210> SEQ ID NO 106
<211> LENGTH: 31
<212> TYPE: PRT
<213> ORGANISM: Human immunodeficiency virus

<400> SEQUENCE: 106

Ile Arg Asn Cys Thr Phe Asn Met Thr Thr Glu Leu Arg Asp Arg Lys
1               5                   10                  15

Lys Gln Val Tyr Ala Leu Phe Tyr Lys Leu Asp Ile Val Pro Ile
            20                  25                  30

<210> SEQ ID NO 107
<211> LENGTH: 31
<212> TYPE: PRT
<213> ORGANISM: Human immunodeficiency virus

<400> SEQUENCE: 107

Met Arg Asn Cys Ser Phe Asn Met Ile Lys Glu Thr Lys Asp Arg Lys
1               5                   10                  15

Gln Lys Val Tyr Ala Thr Phe Tyr Lys Leu Asp Ile Val Pro Ile
            20                  25                  30

<210> SEQ ID NO 108
<211> LENGTH: 31
<212> TYPE: PRT
<213> ORGANISM: Human immunodeficiency virus

<400> SEQUENCE: 108

Val Lys Asn Cys Ser Phe Asn Met Thr Thr Glu Val Thr Asp Lys Lys
1               5                   10                  15

Lys Gln Val His Ala Leu Phe Tyr Arg Leu Asp Ile Val Gln Met
            20                  25                  30

<210> SEQ ID NO 109
<211> LENGTH: 31
<212> TYPE: PRT
<213> ORGANISM: Human immunodeficiency virus

<400> SEQUENCE: 109

Val Arg Asn Cys Thr Phe Asn Val Thr Thr Glu Leu Lys Asp Lys Lys
1               5                   10                  15

Gln Gln Val Tyr Ala Leu Phe Tyr Lys Pro Asp Ile Val Pro Ile
            20                  25                  30

<210> SEQ ID NO 110
<211> LENGTH: 31
<212> TYPE: PRT
<213> ORGANISM: Human immunodeficiency virus

<400> SEQUENCE: 110

Val Lys Asn Cys Ser Phe Ile Met Thr Thr Glu Leu Arg Asp Lys Lys
1               5                   10                  15

Gln Lys Ala Tyr Ala Leu Phe Tyr Met Leu Asp Ile Val Pro Ile
            20                  25                  30

<210> SEQ ID NO 111
<211> LENGTH: 31
<212> TYPE: PRT
<213> ORGANISM: Human immunodeficiency virus

<400> SEQUENCE: 111

Val Met Asn Cys Thr Phe Asn Met Thr Thr Glu Leu Arg Asp Lys Lys
1               5                   10                  15

Lys Gln Val Gln Ala Leu Phe Tyr Lys Leu Asp Met Val Gln Met
            20                  25                  30

<210> SEQ ID NO 112
<211> LENGTH: 31
<212> TYPE: PRT
<213> ORGANISM: Human immunodeficiency virus

<400> SEQUENCE: 112

Val Arg Asn Cys Thr Phe Asn Met Thr Thr Glu Leu Arg Asp Lys Lys
1               5                   10                  15

Arg Lys Val His Ala Leu Phe Tyr Lys Leu Asp Ile Ile Gln Ile
            20                  25                  30

<210> SEQ ID NO 113
<211> LENGTH: 31
<212> TYPE: PRT
<213> ORGANISM: Human immunodeficiency virus

<400> SEQUENCE: 113

```
Val Lys Val Cys Ala Phe Asn Val Thr Thr Glu Ile Lys Asp Lys
1               5                   10                  15

Arg Lys Val His Ala Leu Phe Tyr Lys Leu Asp Ile Val Pro Leu
            20                  25                  30

<210> SEQ ID NO 114
<211> LENGTH: 31
<212> TYPE: PRT
<213> ORGANISM: Human immunodeficiency virus

<400> SEQUENCE: 114

Val Gln Asn Cys Thr Phe Asn Val Thr Thr Glu Leu Ile Asp Lys Gln
1               5                   10                  15

Gln Lys Val Arg Ala Leu Phe Tyr Lys Leu Asp Leu Val Gln Ile
            20                  25                  30

<210> SEQ ID NO 115
<211> LENGTH: 31
<212> TYPE: PRT
<213> ORGANISM: Human immunodeficiency virus

<400> SEQUENCE: 115

Met Arg Asn Cys Ser Phe Asn Met Thr Thr Glu Leu Arg Asp Lys Lys
1               5                   10                  15

Gln Gln Val Tyr Ala Leu Phe Tyr Lys Leu Asp Ile Val Pro Ile
            20                  25                  30

<210> SEQ ID NO 116
<211> LENGTH: 31
<212> TYPE: PRT
<213> ORGANISM: Human immunodeficiency virus

<400> SEQUENCE: 116

Val Lys Asn Cys Thr Phe Asn Met Thr Thr Glu Leu Arg Asp Lys Lys
1               5                   10                  15

Arg Lys Val His Ala Leu Phe Tyr Arg Leu Asp Leu Val Gln Met
            20                  25                  30

<210> SEQ ID NO 117
<211> LENGTH: 31
<212> TYPE: PRT
<213> ORGANISM: Human immunodeficiency virus

<400> SEQUENCE: 117

Val Arg Asn Cys Ser Phe Asn Val Thr Thr Val Leu Gln Asp Lys Lys
1               5                   10                  15

Gln Lys Val His Ala Leu Phe Tyr Arg Leu Asp Leu Val Gln Ile
            20                  25                  30

<210> SEQ ID NO 118
<211> LENGTH: 31
<212> TYPE: PRT
<213> ORGANISM: Human immunodeficiency virus

<400> SEQUENCE: 118

Val Arg Asn Cys Ser Phe Asn Met Thr Thr Val Ile Arg Asp Lys Gln
1               5                   10                  15

Gln Gln Ile His Ala Leu Phe Tyr Lys Leu Asp Ile Val Pro Ile
            20                  25                  30

<210> SEQ ID NO 119
<211> LENGTH: 31
```

<212> TYPE: PRT
<213> ORGANISM: Human immunodeficiency virus

<400> SEQUENCE: 119

Met Arg Asn Cys Ser Phe Asn Met Thr Thr Glu Leu Arg Asp Lys Gln
1               5                   10                  15

Lys Lys Val His Ala Leu Phe Tyr Arg Leu Asp Leu Ala Pro Ile
            20                  25                  30

<210> SEQ ID NO 120
<211> LENGTH: 31
<212> TYPE: PRT
<213> ORGANISM: Human immunodeficiency virus

<400> SEQUENCE: 120

Ile Arg Asn Cys Ser Phe Asn Met Thr Thr Glu Leu Lys Asp Lys Lys
1               5                   10                  15

Gln Lys Val Tyr Ala Leu Phe Tyr Lys Leu Asp Val Val Gln Ile
            20                  25                  30

<210> SEQ ID NO 121
<211> LENGTH: 31
<212> TYPE: PRT
<213> ORGANISM: Human immunodeficiency virus

<400> SEQUENCE: 121

Val Arg Asn Cys Ser Phe Asn Met Thr Thr Glu Ile Lys Asp Lys Lys
1               5                   10                  15

Gln Lys Val His Ala Leu Phe Tyr Lys Leu Asp Ile Val Pro Ile
            20                  25                  30

<210> SEQ ID NO 122
<211> LENGTH: 31
<212> TYPE: PRT
<213> ORGANISM: Human immunodeficiency virus

<400> SEQUENCE: 122

Val Arg Asn Cys Ser Phe Asn Met Thr Thr Glu Ile Arg Asp Lys Lys
1               5                   10                  15

Gln Arg Ile Tyr Ala Leu Phe Tyr Lys Leu Asp Ile Val Pro Ile
            20                  25                  30

<210> SEQ ID NO 123
<211> LENGTH: 31
<212> TYPE: PRT
<213> ORGANISM: Human immunodeficiency virus

<400> SEQUENCE: 123

Val Arg Asn Cys Ser Phe Ser Val Thr Thr Glu Leu Lys Asp Lys Lys
1               5                   10                  15

Gln Lys Val His Ala Leu Phe Tyr Arg Leu Asp Ile Val Gln Met
            20                  25                  30

<210> SEQ ID NO 124
<211> LENGTH: 31
<212> TYPE: PRT
<213> ORGANISM: Human immunodeficiency virus

<400> SEQUENCE: 124

Leu Arg Asn Cys Ser Phe Asn Met Thr Thr Glu Leu Arg Asp Lys Lys
1               5                   10                  15

Gln Lys Val His Ala Leu Phe Tyr Arg Val Asp Met Ile Pro Ile

<210> SEQ ID NO 125
<211> LENGTH: 31
<212> TYPE: PRT
<213> ORGANISM: Human immunodeficiency virus

<400> SEQUENCE: 125

Val Arg Asn Cys Ser Phe Asn Met Thr Thr Val Val Arg Asp Lys Lys
1               5                   10                  15

Gln Lys Val Tyr Ala Leu Phe Tyr Lys Leu Asp Ile Val Pro Ile
            20                  25                  30

<210> SEQ ID NO 126
<211> LENGTH: 31
<212> TYPE: PRT
<213> ORGANISM: Human immunodeficiency virus

<400> SEQUENCE: 126

Val Arg Asn Cys Thr Phe Asn Met Thr Thr Glu Ile Arg Asp Lys Lys
1               5                   10                  15

Gln Lys Ala Tyr Ala Leu Phe Tyr Lys Leu Asp Leu Val Gln Leu
            20                  25                  30

<210> SEQ ID NO 127
<211> LENGTH: 31
<212> TYPE: PRT
<213> ORGANISM: Human immunodeficiency virus

<400> SEQUENCE: 127

Ala Lys Asn Cys Thr Phe Asn Met Thr Thr Glu Leu Arg Asp Lys Gln
1               5                   10                  15

Gln Lys Val Tyr Ala Leu Phe Tyr Asn Leu Asp Ile Val Gln Ile
            20                  25                  30

<210> SEQ ID NO 128
<211> LENGTH: 31
<212> TYPE: PRT
<213> ORGANISM: Human immunodeficiency virus

<400> SEQUENCE: 128

Val Lys Asn Cys Thr Phe Asn Met Thr Thr Glu Leu Thr Asp Lys Lys
1               5                   10                  15

Gln Lys Val His Ala Leu Phe Tyr Lys Leu Asp Ile Val Pro Ile
            20                  25                  30

<210> SEQ ID NO 129
<211> LENGTH: 31
<212> TYPE: PRT
<213> ORGANISM: Human immunodeficiency virus

<400> SEQUENCE: 129

Val Lys Asn Cys Thr Phe Asn Val Thr Thr Glu Leu Lys Asp Lys Lys
1               5                   10                  15

Gln Lys Val Tyr Ala Leu Phe Tyr Lys Leu Asp Ile Val Gln Met
            20                  25                  30

<210> SEQ ID NO 130
<211> LENGTH: 31
<212> TYPE: PRT
<213> ORGANISM: Human immunodeficiency virus

<400> SEQUENCE: 130

```
Val Lys Asn Cys Ser Phe Asn Val Thr Thr Glu Ile Arg Asp Arg Lys
1               5                   10                  15

Gln Lys Ala Tyr Ala Leu Phe Tyr Lys Leu Asp Leu Val Gln Met
            20                  25                  30
```

<210> SEQ ID NO 131
<211> LENGTH: 31
<212> TYPE: PRT
<213> ORGANISM: Human immunodeficiency virus

<400> SEQUENCE: 131

```
Val Lys Asn Cys Thr Phe Asn Met Thr Thr Glu Leu Arg Asp Lys Lys
1               5                   10                  15

Gln Lys Gly Tyr Ala Leu Phe Tyr Lys Leu Asp Ile Val Gln Ile
            20                  25                  30
```

<210> SEQ ID NO 132
<211> LENGTH: 31
<212> TYPE: PRT
<213> ORGANISM: Human immunodeficiency virus

<400> SEQUENCE: 132

```
Val Arg Asn Cys Thr Phe Asn Thr Thr Thr Glu Leu Lys Asp Lys Lys
1               5                   10                  15

Lys Lys Val His Ala Leu Phe Tyr Lys Leu Asp Ile Val Lys Met
            20                  25                  30
```

<210> SEQ ID NO 133
<211> LENGTH: 31
<212> TYPE: PRT
<213> ORGANISM: Human immunodeficiency virus

<400> SEQUENCE: 133

```
Leu Arg Asn Cys Ser Phe Asn Val Thr Thr Glu Leu Arg Asp Arg Gln
1               5                   10                  15

Arg Lys Ala Tyr Ala Leu Phe Tyr Lys Leu Asp Ile Val Pro Ile
            20                  25                  30
```

<210> SEQ ID NO 134
<211> LENGTH: 31
<212> TYPE: PRT
<213> ORGANISM: Human immunodeficiency virus

<400> SEQUENCE: 134

```
Val Arg Asn Cys Ser Phe Asn Met Thr Thr Glu Leu Arg Asp Arg Lys
1               5                   10                  15

Gln Lys Val Tyr Ala Leu Phe Tyr Lys Ile Asp Leu Val Gln Ile
            20                  25                  30
```

<210> SEQ ID NO 135
<211> LENGTH: 31
<212> TYPE: PRT
<213> ORGANISM: Human immunodeficiency virus

<400> SEQUENCE: 135

```
Val Arg Asn Cys Ser Phe Asn Met Thr Thr Glu Leu Gly Asp Lys Lys
1               5                   10                  15

Gln Gln Val Tyr Ala Phe Phe Tyr Asn Leu Asp Leu Val Gln Ile
            20                  25                  30
```

<210> SEQ ID NO 136

```
<211> LENGTH: 31
<212> TYPE: PRT
<213> ORGANISM: Human immunodeficiency virus

<400> SEQUENCE: 136

Met Lys Asn Cys Ser Phe Asn Val Thr Thr Val Ile Arg Asp Lys Lys
1               5                   10                  15

Gln Gln Val His Ala Leu Phe Tyr Lys Leu Asp Ile Val Arg Met
            20                  25                  30

<210> SEQ ID NO 137
<211> LENGTH: 31
<212> TYPE: PRT
<213> ORGANISM: Human immunodeficiency virus

<400> SEQUENCE: 137

Ile Arg Asn Cys Thr Phe Asn Met Thr Thr Glu Ile Arg Asp Lys Lys
1               5                   10                  15

Gln Met Val His Ala Leu Phe Tyr Lys Leu Asp Ile Val Glu Met
            20                  25                  30

<210> SEQ ID NO 138
<211> LENGTH: 31
<212> TYPE: PRT
<213> ORGANISM: Human immunodeficiency virus

<400> SEQUENCE: 138

Val Lys Asn Cys Ser Phe Asn Thr Thr Thr Glu Leu Arg Asp Lys Lys
1               5                   10                  15

Lys Lys Ser Tyr Ala Leu Phe Tyr Lys Leu Asp Ile Val Pro Ile
            20                  25                  30

<210> SEQ ID NO 139
<211> LENGTH: 31
<212> TYPE: PRT
<213> ORGANISM: Human immunodeficiency virus

<400> SEQUENCE: 139

Val Lys Asn Cys Ser Tyr Asn Met Thr Thr Glu Ile Lys Asp Lys Lys
1               5                   10                  15

Gln Lys Val His Ser Leu Phe Tyr Arg Leu Asp Ile Val Pro Ile
            20                  25                  30
```

What is claimed is:

1. A method of inducing an immune response in a subject comprising administering to the subject a composition comprising a recombinant HIV-1 polypeptide comprising: all the consecutive amino acids immediately after the signal peptide in an HIV-1 envelope AA 104.0 (amino acid positions 30-846 in SEQ ID NO: 1), all the consecutive amino acids immediately after the signal peptide in an HIV-1 envelope AA 107.0 (amino acid positions 30-861 in SEQ ID NO: 2), all the consecutive amino acids immediately after the signal peptide in an HIV-1 envelope AA 058.1 (amino acid positions 30-856 in SEQ ID NO: 3), or a combination thereof in an amount sufficient to effect induction, wherein each HIV-1 polypeptide is recombinantly produced.

2. A method of inducing an immune response in a subject comprising administering to the subject a composition comprising:
   AA 104.0 gp120Delta N-terminus recombinant polypeptide comprising all the consecutive amino acids at amino acid positions 41-501 in SEQ ID NO:1,
   AA 107.0 gp120Delta N-terminus recombinant polypeptide comprising all the consecutive amino acids at amino acid positions 41-509 in SEQ ID NO: 2, or
   AA 058.1 gp120Delta N-terminus recombinant polypeptide comprising all the consecutive amino acids at amino acid positions 41-511 in SEQ ID NO:3 in an amount sufficient to effect induction, wherein each HIV-1 polypeptide is recombinantly produced.

3. A method of inducing an immune response in a subject comprising administering to the subject a composition comprising:
   AA 104.0 gp120Delta N-terminus recombinant polypeptide, comprising all the consecutive amino acids at amino acid positions 41-501 in SEQ ID NO: 1,
   AA 107.0 gp120Delta N-terminus recombinant polypeptide comprising all the consecutive amino acids at amino acid positions 41-509 in SEQ ID NO: 2, and
   AA 058.1 gp120Delta N-terminus recombinant polypeptide comprising all the consecutive amino acids at amino acid positions 41-511 in SEQ ID NO:3, in an amount sufficient to effect induction, wherein each HIV-1 polypeptide is recombinantly produced.

4. A method of inducing an immune response in a subject comprising administering to the subject a composition comprising AA 104.0 gp120Delta N-terminus recombinant polypeptide, comprising all the consecutive amino acids at amino acid positions 41-501 in SEQ ID NO: 1 in an amount sufficient to effect induction, wherein the HIV-1 polypeptide is recombinantly produced.

5. The method of claim 1 or 2-4 further comprising administration of HIV-1 envelope B.63521 gp120D11 and A244 gp120 D11.

6. The method of claim 1 or 2-4 further comprising administration of HIV-1 envelope B.6240 gp120D11 and A244 gp120 D11.

7. The method of claim 1 or claim 2-4, wherein the composition further comprises an adjuvant.

8. The method of claim 7, wherein the adjuvant is a Toll-like receptor 4 agonist glucopyranosyl lipid adjuvant-stable emulsion (GLA/SE).

9. The method of claim 1 or 2-4, wherein the composition is administered as a boost.

10. The method of claim 2, wherein the composition is administered as a boost.

11. The method of claim 3, wherein the composition is administered as a boost.

12. The method of claim 4, wherein the composition is administered as a boost.

* * * * *